US010590457B2

(12) United States Patent
Tian et al.

(10) Patent No.: US 10,590,457 B2
(45) Date of Patent: Mar. 17, 2020

(54) COMPOSITIONS FOR CELL CULTURE AND METHODS OF USING THE SAME

(71) Applicant: BRISTOL-MYERS SQUIBB COMPANY, Princeton, NJ (US)

(72) Inventors: Jun Tian, Westford, MA (US); Jianlin Xu, Littleton, MA (US); Qin He, Littleton, MA (US)

(73) Assignee: BRISTOL MYERS-SQUIBB COMPANY, Princeton, NJ (US)

( * ) Notice: Subject to any disclaimer, the term of this patent is extended or adjusted under 35 U.S.C. 154(b) by 0 days.

(21) Appl. No.: 15/549,760

(22) PCT Filed: Feb. 11, 2016

(86) PCT No.: PCT/US2016/017432
§ 371 (c)(1),
(2) Date: Aug. 9, 2017

(87) PCT Pub. No.: WO2016/130734
PCT Pub. Date: Aug. 18, 2016

(65) Prior Publication Data
US 2018/0044709 A1 Feb. 15, 2018

Related U.S. Application Data

(60) Provisional application No. 62/114,635, filed on Feb. 11, 2015.

(51) Int. Cl.
C12P 21/02 (2006.01)
C12Q 1/04 (2006.01)
C12N 5/00 (2006.01)

(52) U.S. Cl.
CPC ............ C12P 21/02 (2013.01); C12N 5/0018 (2013.01); C12Q 1/04 (2013.01)

(58) Field of Classification Search
None
See application file for complete search history.

(56) References Cited

U.S. PATENT DOCUMENTS

| 5,721,121 A | 2/1998 | Etcheverry et al. |
| 2014/0329279 A1* | 11/2014 | Wang ................. C07K 16/241 435/69.6 |
| 2016/0037411 A1 | 2/2016 | Franklin et al. |

FOREIGN PATENT DOCUMENTS

| WO | WO1986/05807 A1 | 10/1986 |
| WO | WO1987/04462 A1 | 7/1987 |
| WO | WO1989/01036 A1 | 2/1989 |
| WO | WO1989/10404 A1 | 11/1989 |
| WO | WO1991/06657 A1 | 5/1991 |
| WO | WO2001/92337 A2 | 12/2001 |
| WO | WO 2007/067564 A2 | 6/2007 |
| WO | WO 2010/071800 A1 | 6/2010 |
| WO | WO 2010/121208 A3 | 10/2010 |
| WO | WO 2011/050286 A1 | 4/2011 |
| WO | WO 2014/182658 A1 | 11/2014 |

OTHER PUBLICATIONS

Zhang et al. Cell Biology International, vol. 32, Issue 6, Jun. 2008, pp. 654-662 (Year: 2008).*
Chkhikvishvili et al. Oxidative Medicine and Cellular Longevity, vol. 2013, Article ID 456253, 9 pages (Year: 2013).*
Kim, Kyung-Chan, et al., "Axl receptor tyrosine kinase is a novel target of apigenin for the inhibition of cell proliferation", International Journal of Molecular Medicine, Aug. 2014, vol. 34, No. 2, pp. 592-598.
Yoon, Man-Soo, et al., "Apigenin Inhibits Immunostimulatory Function of Dendritic Cells: Implication of Immunotherapeutic Adjuvant", Molecular Pharmacology, Sep. 2006, vol. 70, No. 3, pp. 1033-1044.
Barnes David, "Serum-free Cell Culture: a Unifying Approach", Cell, vol. 22-649-655 (1980).
Bebbington, et al., "The use of vectors based on gene amplification for the expression of cloned genes in mammalian cells in DNA cloning", DNA Cloning: A Practical Approach vol. 3 pp. 163-188 (1987).
Crouse, Gray F. et al., "Expression and Amplification of Engineered Mouse Dihydrofolate Reductase Minigenes", Molecular and Cellular Biology, vol. 3(2), pp. 257-266 (1983).
Fiers, W. et al., "Complete nucleotide sequence of SV40 DNA", Nature, vol. 273 pp. 113-120 (1978).
Graham, F.L. et al., "Characteristics of a Human Cell Line Transformed by DNA from Human Adenovirus Type 5", J. Gen. Virology., vol. 36, pp. 59-74 (1977).
Karin, M. et al., "Human metallothionein genes—primary structure of the metallotheonein-II gene and a related processed gene", Nature, vol. 299, pp. 797-802 (1982).
Kriegler, Michael Gene Transfer and Expression, A Laboratory Manual, Stockton Press, NY (1990).
Lowy, Israel et al., "Isolation of Transforming DNA: Cloning the Hamster aprt Gene", Cell, vol. 22, pp. 817-823 (1980).
Mather, Jennie P., "Establishment and Characterization of Two Distinct Mouse Testicular Epithelial Cell Lines", Biology of Reproduction, vol. 23, pp. 243-252 (1980).
Mather, Jennie P., Culture of Testicular Cells in Hormone-supplemented serum-free medium, Annals NY Academy Science, vol. 383, pp. 44-68 (1982).
Mulligan, B.C. et al., "Selection for animal cells that express the *Escherichia coli* gene coding for xanthine-guanine phosphoribosyltransferase", PNAS, vol. 78(4), pp. 2072-2076 (1981).
Sambrook, J. et al., Molecular Cloning, A Laboratory Manual, Cold Spring Harbor Press, Plainview, NY (1989).

(Continued)

Primary Examiner — Christian L Fronda
(74) Attorney, Agent, or Firm — Z. Angela Guo

(57) ABSTRACT

The present invention relates to new methods and processes for culturing mammalian cells with the addition of phenolic antioxidants. Performance of the cell culturing methods and processes in their various aspects result in a higher viable cell density and higher protein titer.

18 Claims, 28 Drawing Sheets

(56) References Cited

OTHER PUBLICATIONS

Santerre, Robert F., et al., "Expression of prokaryotic genes for hygromycin B and G418 resistance as dominant-selection markers in mouse L cells", Gene, vol. 30 pp. 147-156 (1984).

Stephens, P.E. et al., "The construction of a highly efficient and versatile set of mammalian expression vectors", Nucleic Acids Research, vol. 17(17), pp. 7110 (1989).

Subramani, S. et al., "Expression of the Mouse Dihydrofolate Reductase Complementary Deoxyribunucleic Acid in Simian Virus 40 Vectors", Molecular and Cellular Biology, vol. 1(9), pp. 854-864 (1981).

Swift, Galvin H., "Tissue-Specific Expression of the Rat Pancreatic Elastase I Gene in Transgenic Mice", Cell, vol. 38, pp. 639-646 (1984).

Szybalska, E.H. et al., "Genetics of Human Cell Lines, IV. DNA-Mediated Heritable Transformation of a Biochemical Trait", PNAS, vol. 48, pp. 2026-2034 (1992).

Yun, Z. et al., "Combined Addition of Glutathione and Iron Chelators for Decrease of Intracellular Level of Reactive Oxygen Species and Death of Chinese Hamster Ovary Cells", J. of Bioscience and Bioengineering, vol. 95(2), pp. 124-127 (2003).

Yun, Z. et al., "Effect of Antioxidants on the Apoptosis of CHO Cells and Production of Tissue Plasminogen Activator in Suspension Culture", J. of Bioscience and Bioengineering, vol. 91(6), pp. 581-585 (2001).

Wigler, M. et al., "Transformation of mammalian cells with an amplifiable dominant-acting gene", PNAS, vol. 77(6), pp. 3567-3570 (1980).

Wigler, M. et al., "Transfer of Purified Herpes Virus Thymidine Kinase Gene to Cultured Mouse Cells", Cell, vol. 11, pp. 223-232 (1977).

Wu, George Y. et al., "Delivery systems for gene therapy", Biotherapy, vol. 3, pp. 87-95 (1991).

\* cited by examiner

B

A

C

D

A c

D

A

A

A

C

COMPOSITIONS FOR CELL CULTURE AND METHODS OF USING THE SAME

CROSS-REFERENCE TO RELATED APPLICATIONS

This application claims priority to U.S. Provisional Application Ser. No. 62/114,635, filed Feb. 11, 2015; the entire content of which is incorporated herein by reference.

FIELD OF THE INVENTION

The present invention relates to new methods and processes for culturing mammalian cells with the addition of antioxidants. Performance of the cell culturing methods and processes in their various aspects result in a higher viable cell density and higher protein titer.

INTRODUCTION

Current ongoing efforts to maximize bioreactor productivity in both time and volume directly affect the scale and capital investment required for a bioreactor suite. As cells reach higher concentrations more quickly, yield is increased; therefore, the number and scale of bioreactors can be reduced. To that end, not only cell engineering, but also culture media and related chemical and physical environments are used to assist cells in reaching peak performance quickly and maintaining a high level as long as possible.

Removing or reducing reactive oxygen species (ROS) such as superoxide anions, hydrogen peroxide, hydroxyl radicals, or singlet oxygen has been shown to improve productivity, presumably through reduction of apoptosis. Yun et al. showed with Chinese Hamster Ovary (CHO) culture that a combination of glutathione and iron chelators decreased intracellular ROS levels and increased the number of viable cells ("Combined Addition of Glutathione and Iron Chelators for Decrease of Intracellular Level of Reactive Oxygen Species and Death of Chinese Hamster Ovary Cells", *J. Biosci. Bioeng.*, 95:124-127 (2003)). Addition of specific iron chelator combinations also reduced ROS and yielded improved viability. Adding several together was more effective than adding single chelators separately. Similar results were reported upon addition of ascorbic acid and glutathione as antioxidants to CHO culture by Yun et al. ("Effect of Antioxidants on the Apoptosis of CHO Cells and Production of Tissue Plasminogen Activator in Suspension Culture", *J. Biosci. Bioeng.*, 91:581-585 (2001)).

Antioxidants commonly used during cell culture include tocopherol, transferrin, selenium, ascorbate and reduced glutathione. Tocopherol is a membrane antioxidant with low solubility in water that functions to neutralize lipid peroxides. Transferrin is a chelator that binds iron with such high affinity leaving no iron available to generate free radicals. Transferrin serves as an extracellular iron transporter and storage molecule. Glutathione is a water-soluble antioxidant tripeptide, which contains a reducing thiol group. It is ubiquitously produced in all cell types and is important for cell proliferation and viability. Selenium is a component of the antioxidant enzymes glutathione peroxidase and thioredoxin reductase which reduce glutathione and thioredoxin, respectively. Ascorbate is a water-soluble antioxidant that regenerates reduced tocopherol. Most commercially-available basal mediums do not contain antioxidants as they were designed for use in conjunction with serum. The serum would typically provide the required antioxidants.

Recombinantly produced protein products are increasingly becoming medically and clinically important for use as therapeutics, treatments and prophylactics. Therefore, the development of reliable cell culture processes that economically and efficiently achieve an increased viable cell density thereby resulting in increased final protein product concentration fulfills both a desired and needed goal in the art.

SUMMARY OF THE INVENTION

The present invention provides new processes for the production of proteins by animal or mammalian cell cultures. These new processes achieve increased viable cell density, cell viability and productivity.

The inventors have identified suitable phenolic antioxidants over a range of concentrations, in different chemically defined basal and feed media, in small and large scale cell culture using different transfected cell lines that produce antibody or fusion proteins.

On aspect of the invention concerns the growth of cells in antioxidant supplemented culture media. More specifically, the cells are Chinese hamster Ovary cells and the antioxidant is added to the basal or feed media, or both the basal and feed media.

Another aspect of the method of this invention concerns the selection of phenolic antioxidant from the group consisting of apigenin, catechin, chlorogenic acid, daidzein, genistein, hesperetin, melatonin, naringenin, pelargonidin, quercetin, resveratrol, rosmarinic acid and silibinin. More specifically, one or more antioxidant is selected from catechin, chlorogenic acid, pelargonidin, quercetin, resveratrol, rosmarinic acid or silibinin. More specifically, the antioxidant utilized in the method of this invention is catechin or rosmarinic acid.

Another aspect of the method of this invention concerns the amount of antioxidant added to the cell culture. An amount of antioxidant suitable for use in the basal and/or feed medium comprises from about 0.0625 mM to about 1 mM. More specifically, the amount of antioxidant suitable for use in the basal media comprises the lower end of the suitable range, for example, from about 0.0625 mM to 0.25 mM. The amount of antioxidant suitable for the feed media comprises the upper end of the suitable range, for example, from about 0.25 mM to 1 mM.

DETAILED DESCRIPTION OF THE INVENTION

Figure 1:
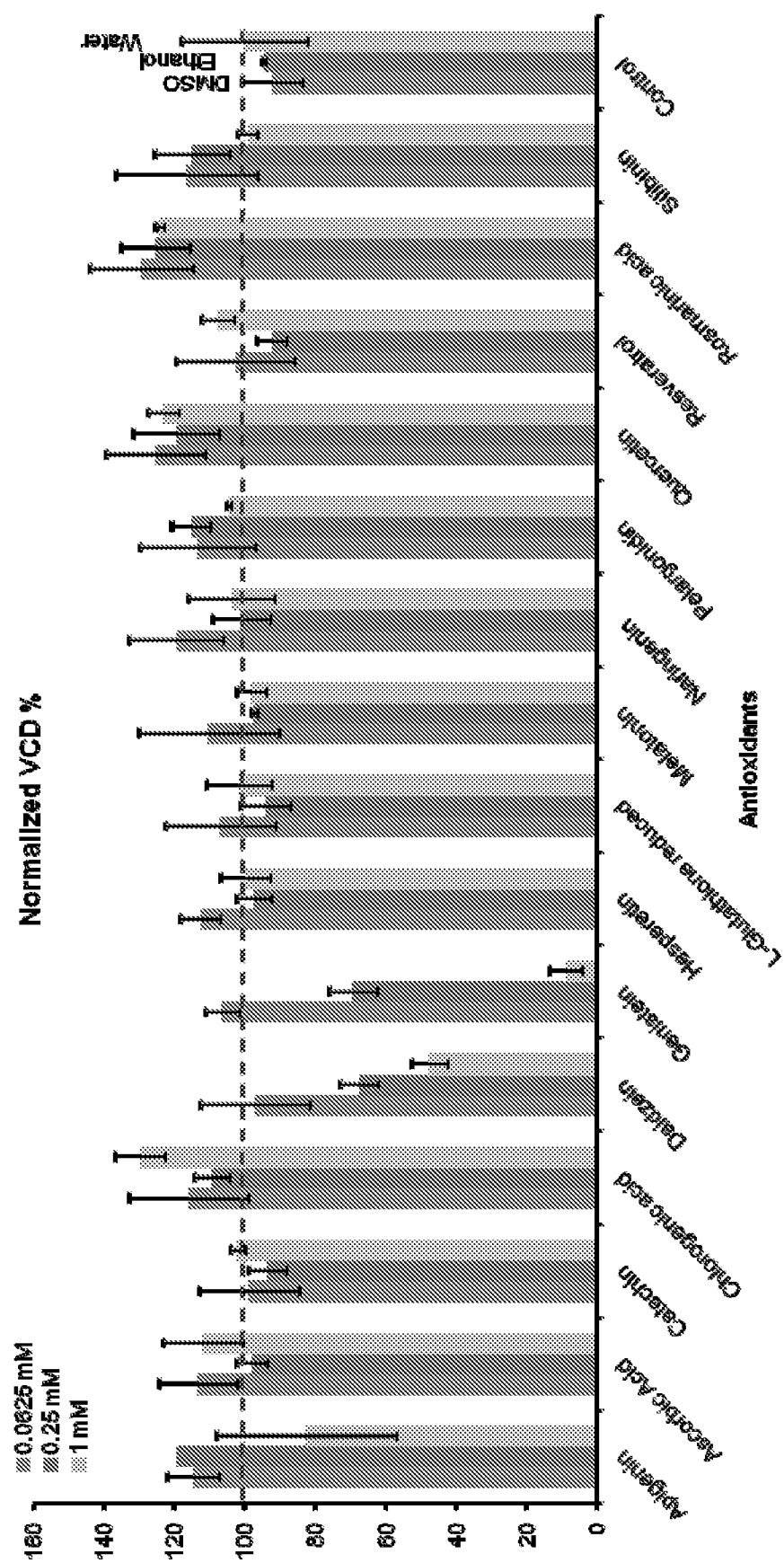
FIG. 1 shows the impact of 0.0625 mM, 0.25 mM and 1 mM of different antioxidants added to the feed media M154A1B on aCD137 viable cell density (VCD) at day 8 (peak VCD). The basal media M17IB was not supplemented with antioxidant. The cell density for each condition was normalized to the control condition with no additional antioxidants in the feed.

This invention is directed to an enhanced process (method) for the preparation of recombinant proteins by mammalian cell cultures, specifically CHO cell cultures, in which the viable cell density and protein titer are increased by the use of a newly-described media strategy in which antioxidants are added to the cell cultures. The antioxidants are provided to the cell cultures in an amount that is effective for attaining and maintaining viable cell density and therefore maximizing protein production until the end of a culturing run. As described herein, a variety of antioxidant supplementation regimens are encompassed by the present invention.

Culturing Processes Involving Antioxidant Addition

In accordance with this invention, the addition of antioxidants to the cell culture increases and/or maintains viable cell density during the production run. The presence of an effective amount of antioxidants in the basal media and/or over the course of the culturing process was found to result in an increased protein titer. To maintain and/or sustain the viable cell density antioxidants are added to the basal and or feed media. The processes and methods of the present invention are suited to both small (e.g., 50 L-100 L) and large scale (e.g., 500 L and greater) cell cultures. In addition, the methods of the present invention are particularly suited to cells grown and maintained as fed-batch cultures, of both small and large scale. In addition, a variety of culture media as known in the art can be used in the culturing methods of this invention.

An antioxidant is a molecule that inhibits the oxidation of other molecules. Oxidation is a chemical reaction that transfers electrons or hydrogen from a substance to an oxidizing agent. Oxidation reactions can produce free radicals. In turn, these radicals can start chain reactions. When the chain reaction occurs in a cell, it can cause damage or death to the cell. Antioxidants terminate these chain reactions by removing free radical intermediates, and inhibit other oxidation reactions. They do this by being oxidized themselves, so antioxidants are often reducing agents such as thiols, ascorbic acid, or polyphenols.

A polyphenol antioxidant is a type of antioxidant containing a polyphenolic or natural phenol substructure. Although all polyphenols have similar chemical structures, there are some distinctive differences. Based on these differences polyphenols are subdivided into several major subclasses including: phenolic acids (such as rosmarinic acid and chlorogenic acid), stilbens (such as resveratrol), tannins, flavonolignans (such as silibinin) and flavonoids.

Flavonoids are the largest family of poly phenolic antioxidants. Flavonoids are further divided in several subclasses including: anthocyanins such as pelargonidin), flavanols (such as catechin), flavanones (such as naringenin and hesperetin), flavonols (such as quercetin), flavones (such as apigenin), and isoflavones (such as genistein and daidzein).

An advantage of the present invention is that protein production costs are reduced by the increase in protein production as achieved by the culturing methods described herein. In a preferred embodiment, higher viable cell density was maintained throughout the culture run when antioxidants were included in the basal and/or feeding medium supplied to the cell culture as shown in FIGS. 1-9.

One embodiment of the invention involves the addition of antioxidant to the basal media to allow for the production of large amounts of protein independent of the reactor scale as shown in FIGS. 5, 6, 7 and 8.

One embodiment of the invention involves the maintenance of the antioxidant feeding strategy throughout a production run, preferably, with daily feeding, to allow for the production of large amounts of protein independent of the reactor scale as shown in FIGS. 1, 2, 4, 7 and 9.

Figure 3:
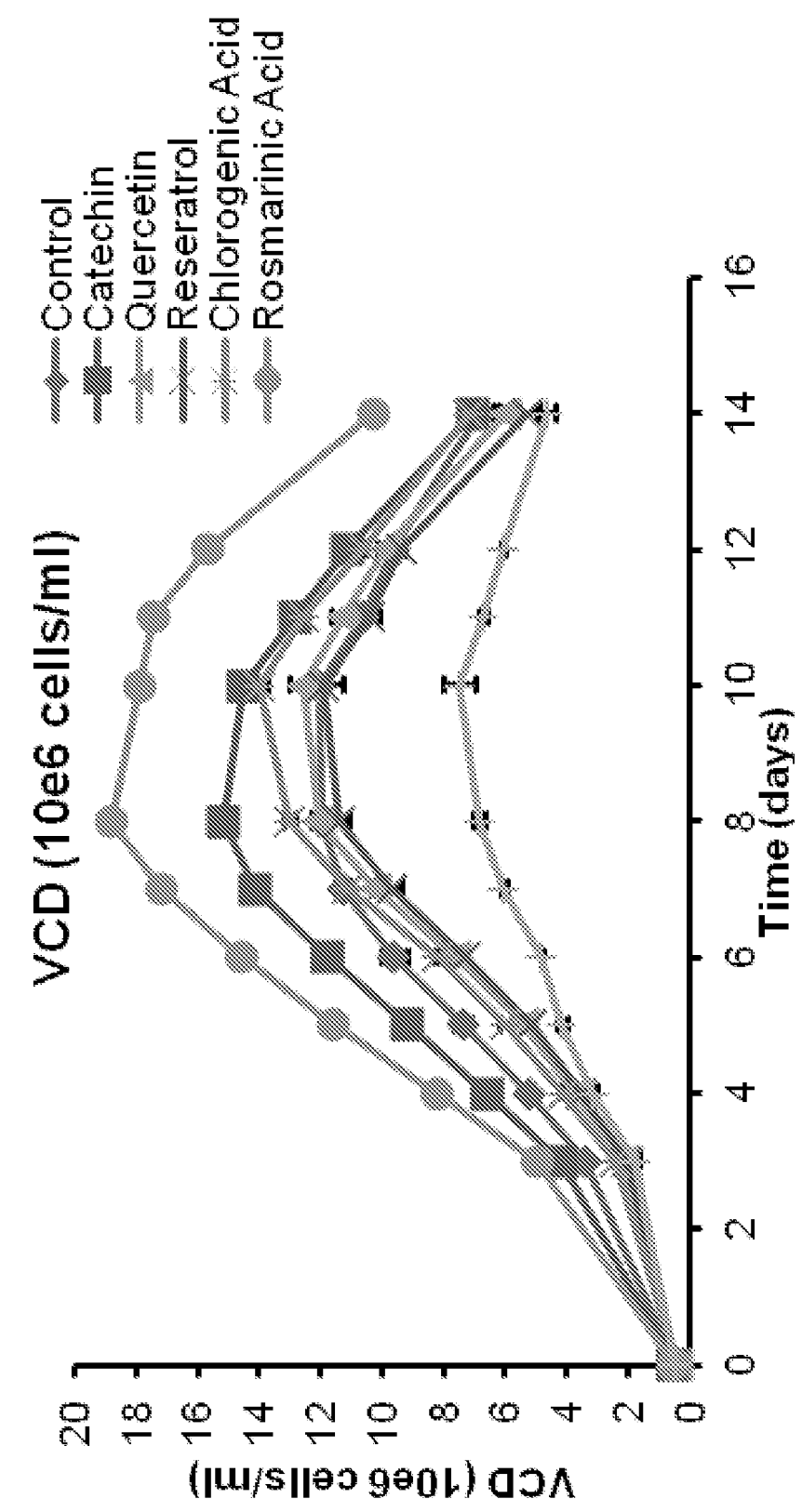
FIG. 3A-C show the impact of catechin, chlorogenic acid, quercetin, resveratrol and rosmarinic acid on aCD137 cell culture (A) viable cell density, (B) normalized protein titer, and (C) lactate concentration. The antioxidants were added to basal media M17IB at 0.07 mM and feed media M154A1B at 1 mM. The media were then used in a standard shaker flask fed-batch culture with aCD137 cells.
Figure 3:
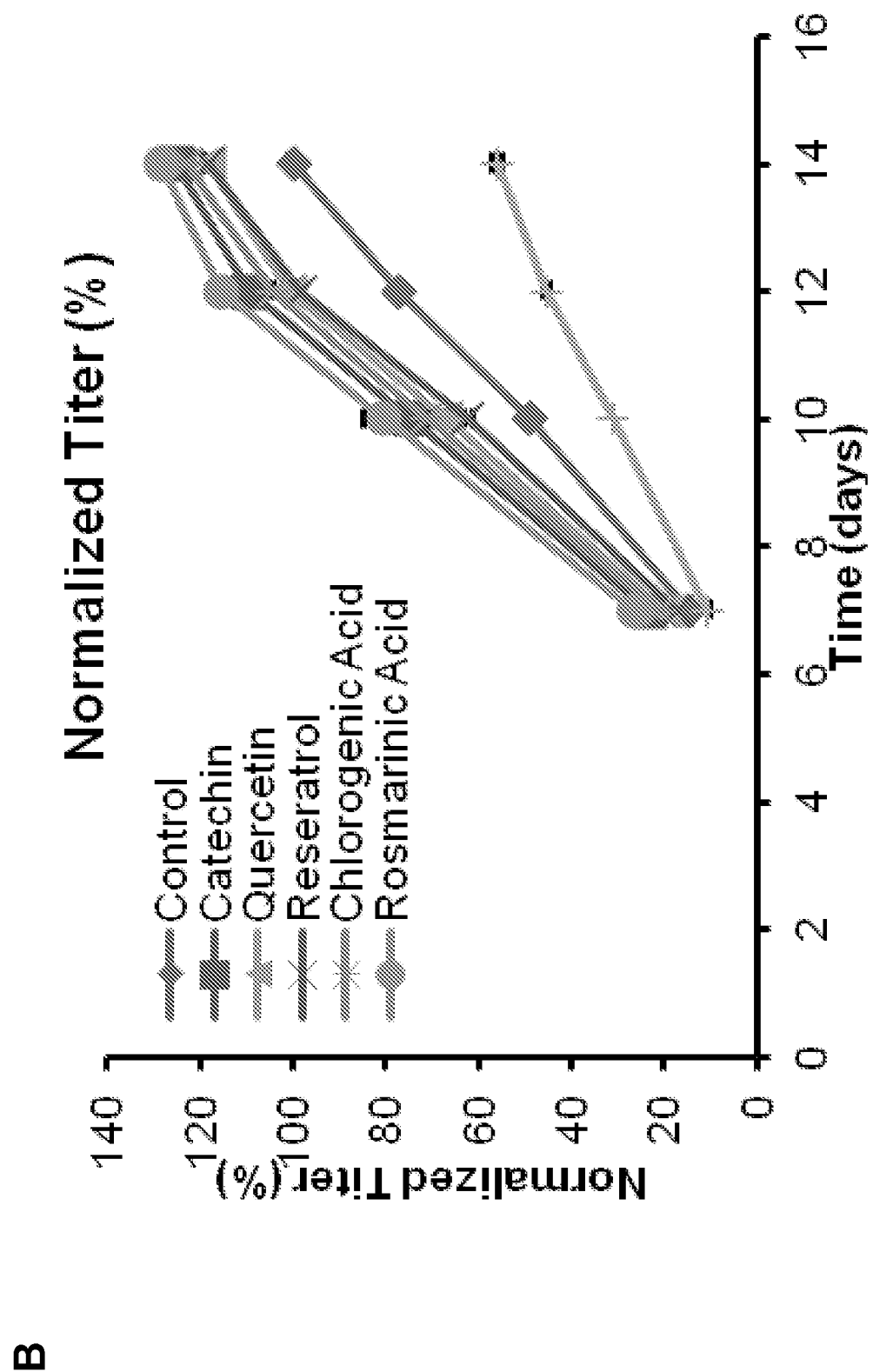
Figure 3:
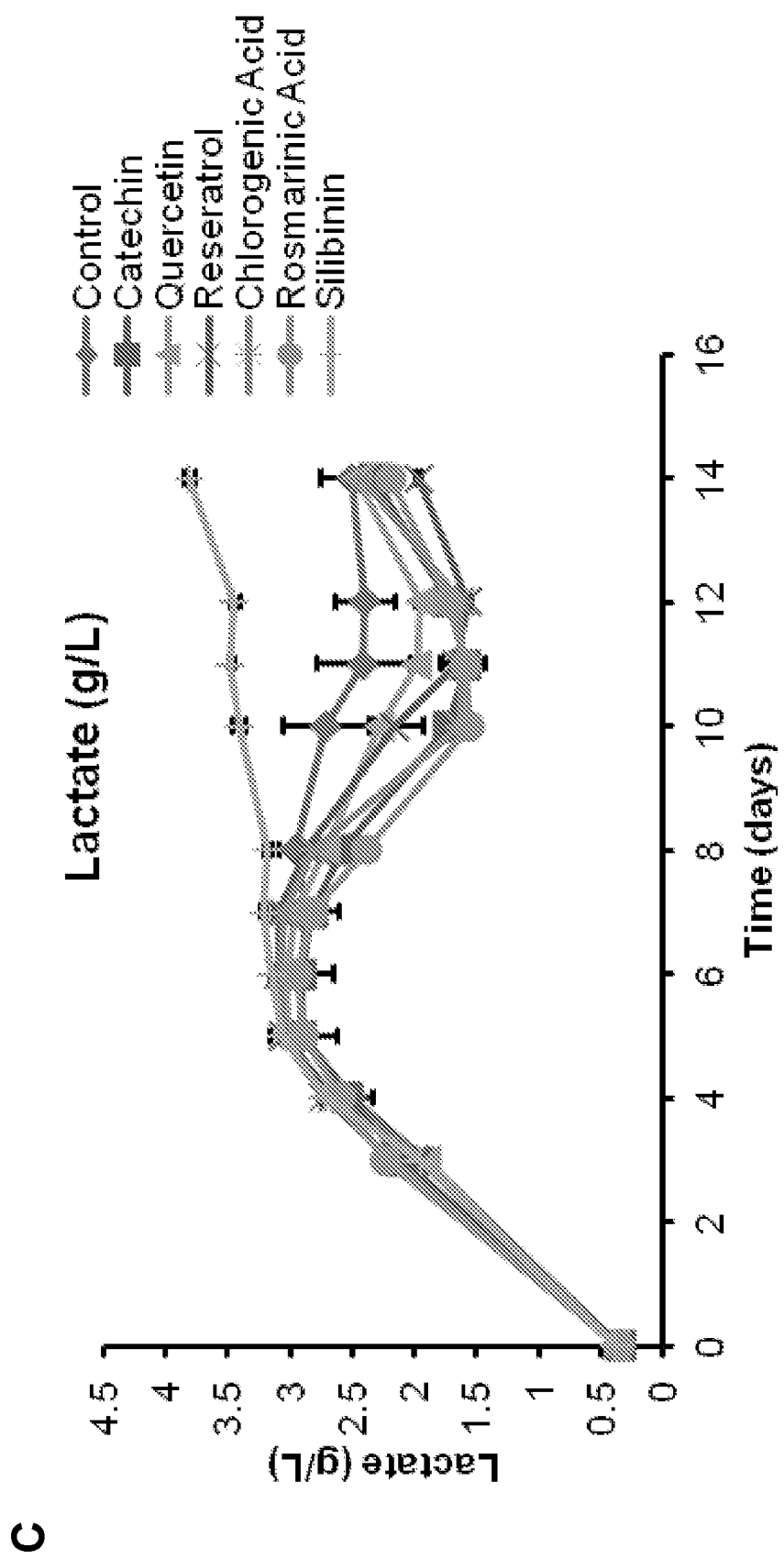
Figure 7:
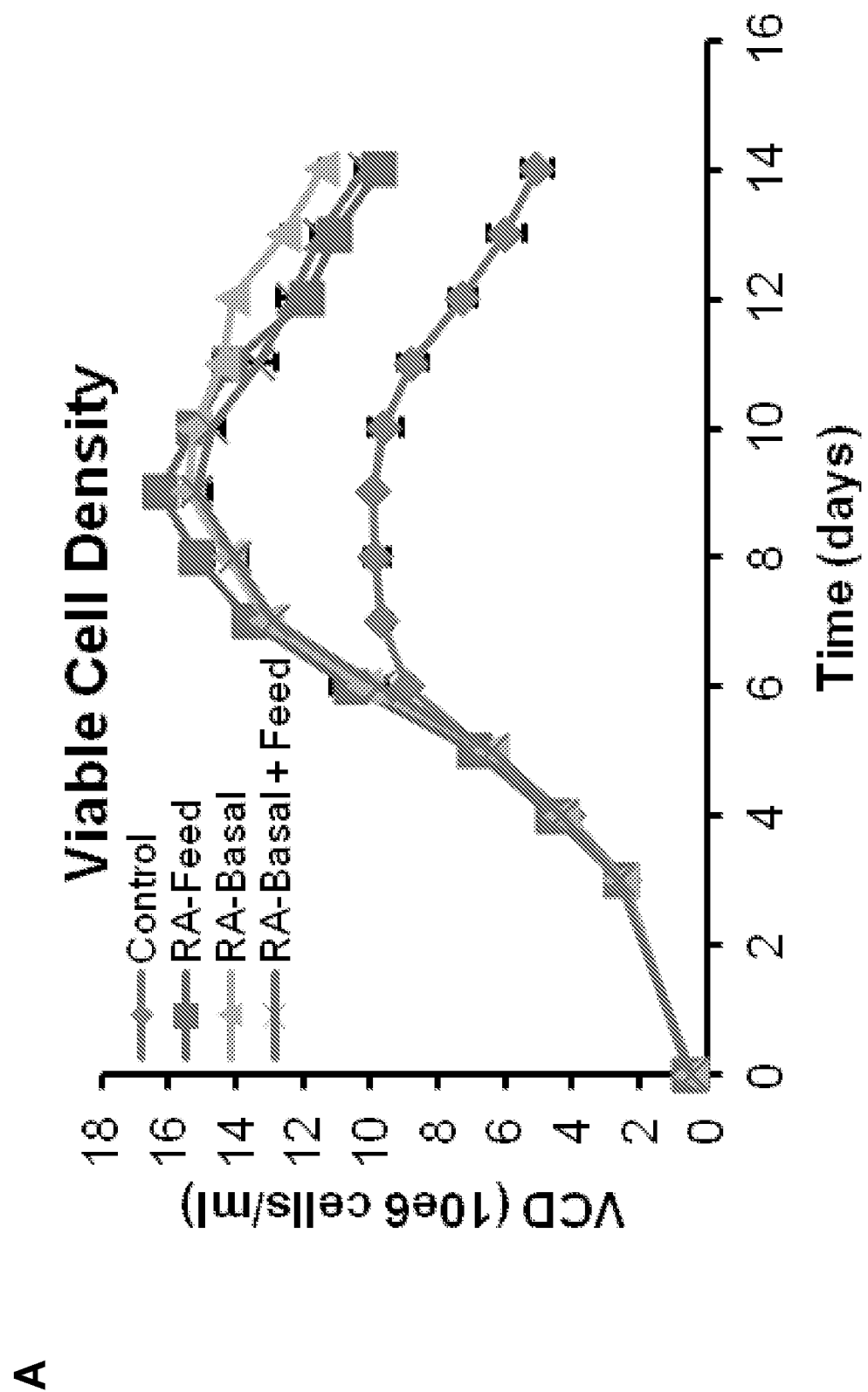
FIG. 7A-D shows the impact of rosmarinic acid addition to either basal media B1 at 0.1 mM (RA-Basal) or feed media F3.2 at 1 mM (RA-Feed), or both (RA-Basal+Feed) on (A) viable cell density, (B) cell viability, (C) normalized protein titer and (D) ammonium concentration. The media was then used in a standard shake flask with myostatin cells.
Figure 7:
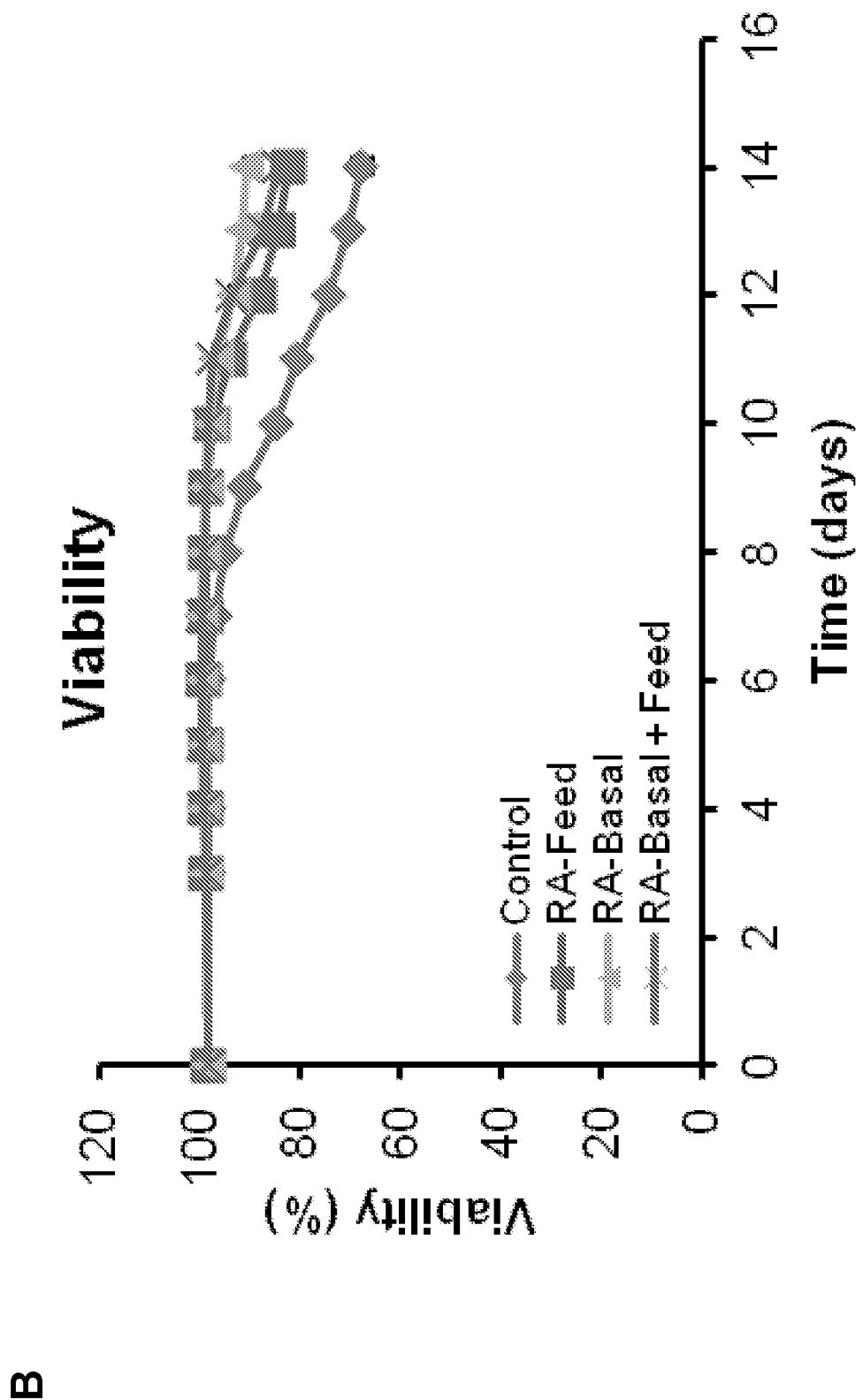
Figure 7:
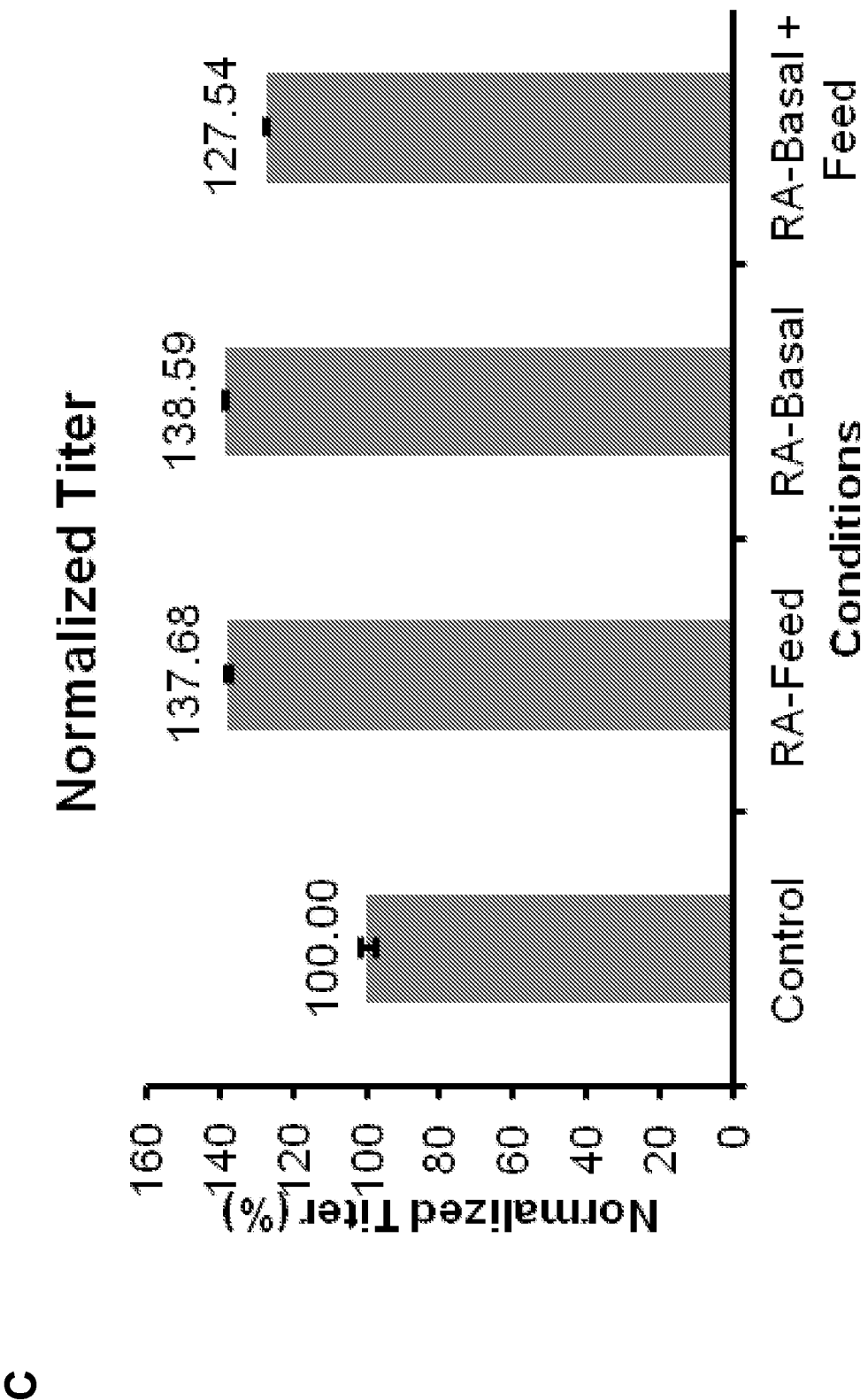
Figure 7:
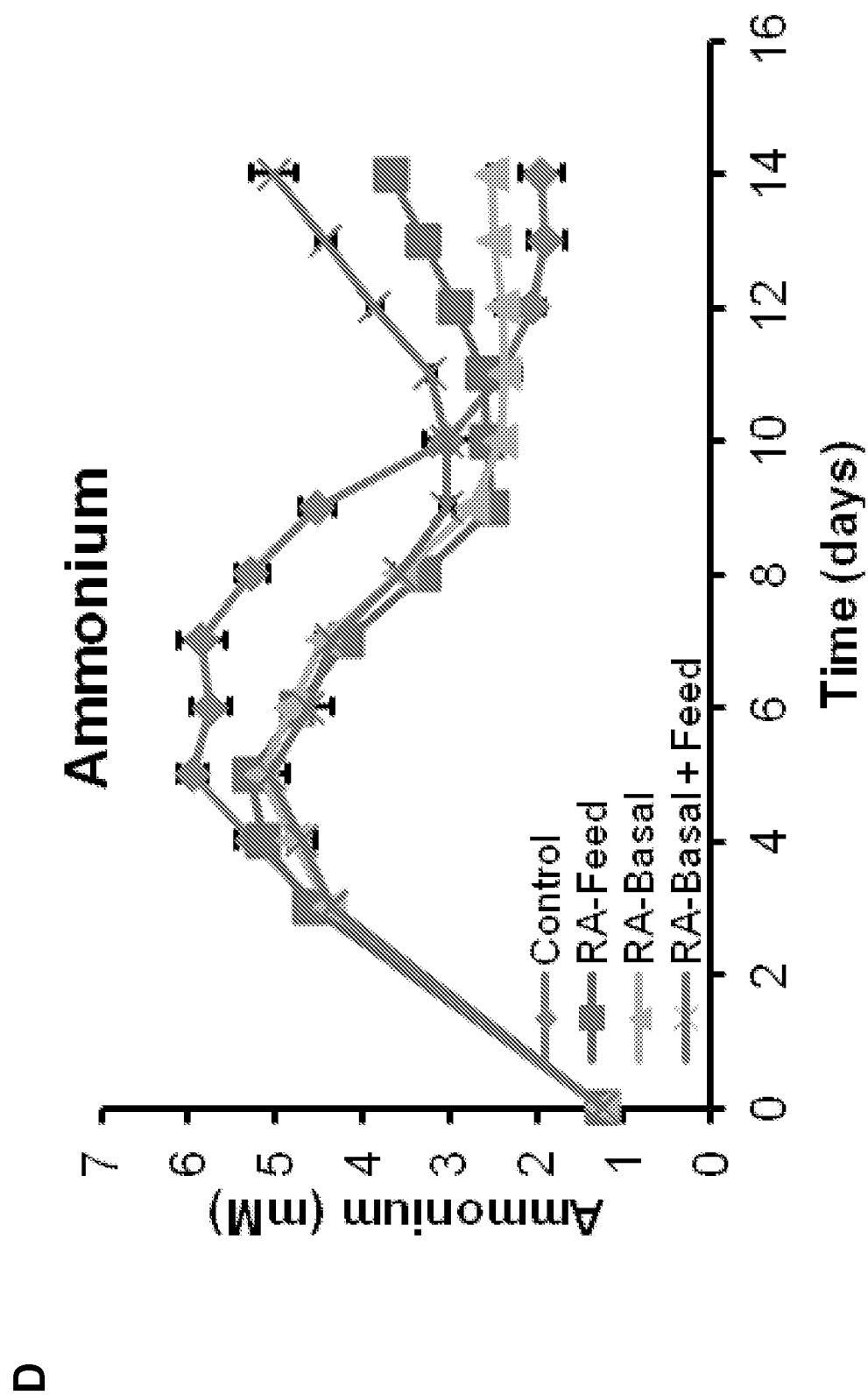

One embodiment of the invention involves the addition of antioxidant to the basal and feed media to allow for the production of large amounts of protein independent of the reactor scale as shown in FIGS. 3 and 7.

An effective concentration of antioxidants as a component in a basal or feed media, increases, maintains and/or sustains viable cell density throughout the production run. The type and amount of antioxidant suitable for use in the basal or feed medium can be determined by the skilled practitioner based on the reactor size and volume of the culture. The methods of the present invention are suitable for all reactor scales at which protein production occur, including, but not limited to, large and small production scale, and reactor scale, e.g., large scale cultures or commercial scale cultures, e.g., over 50 L, more preferably over 500 L. For example, the antioxidant supplementation strategy is applicable for production scale cultures, e.g., having a volume of about 50 liters (50 L) or less, as well as for reactor scale cultures, which can have a volume of several hundreds or thousands of liters.

In accordance with the methods of this invention, one or more antioxidant is selected from the group consisting of apigenin, catechin, chlorogenic acid, daidzein, genistein, hesperetin, melatonin, naringenin, pelargonidin, quercetin, resveratrol, rosmarinic acid and silibinin; preferably, one or more antioxidant is selected from catechin, chlorogenic acid, pelargonidin, quercetin, resveratrol, rosmarinic acid and silibinin; more preferably, one or more antioxidant is selected from catechin, chlorogenic acid, quercetin, resveratrol and rosmarinic acid; more preferably, the antioxidant is catechin or rosmarinic acid.

In accordance with the methods of this invention, basal or feed medium concentration of one or more of the antioxidants selected from the list above is preferably provided in an amount which affords a higher sustained or maintained viable cell density in the culture, or reactor, during the culturing process. An amount of antioxidant suitable for use in the basal and/or feed medium comprises from about 0.0625 mM to about 1 mM, preferably about 0.1 mM to about 1 mM. More specifically, the amount of antioxidant suitable for use in the basal media comprises the lower end of the suitable range, for example, from about 0.0625 mM to 0.25 mM, and the amount of antioxidant suitable for the feed media comprises the upper end of the suitable range, for example, from about 0.25 mM to 1 mM.

As specific yet nonlimiting examples, 1 mM catechin in the feed medium is suitable for use in the culturing method of the invention; or 0.1 mM rosmarinic acid or catechin in the basal media is suitable for use in the culturing method of the invention; or 0.1 mM rosmarinic acid in the basal media and 1 mM rosmarinic acid in the feed media is suitable for use in the culturing method of the invention.

Cell cultures are fed with feeding medium containing antioxidants of the invention using a variety of feeding schedules or regimens to deliver and maintain the antioxidants in the cultures in amounts that sustain a viable cell density effective antioxidant concentration thereby increasing protein production. In general, the culturing methods of the present invention comprise the feeding of cell cultures with the antioxidants of the invention in the feeding medium more than one time during the culture run. It is to be understood that the culture volume contributed by the feeding medium at the end of a culture run typically comprises approximately 30-60% of the original culture volume.

The cell cultures can be fed the antioxidants of the invention on a daily basis, or on other than a daily basis, e.g., less often than once per day, and at varying intervals, preferably timed intervals, including every other day, every third day, every fourth day, and the like. For example, the feeding of cell cultures with the antioxidants of the invention, preferably with antioxidant-containing feeding medium, can be performed once per day, more than once per day, or less than once per day, and can occur one time, two times, or more than two times, e.g., three, four, five or more times, during the total culture run. In one embodiment, the cells are fed with antioxidants more than once.

Also encompassed by this invention is a continuous feeding schedule, for example, involving a continuous infusion of the antioxidants of the invention, preferably an antioxidant-containing feeding medium, into the cultures. In such a continuous feeding regimen, the cultures receive antioxidants, preferably in feeding medium, for example, as a continuously-supplied "drip", or infusion, or other automated addition to the culture, in a timed, regulated, and/or programmed fashion so as to achieve and maintain the appropriate amount of antioxidant in the culture. Most preferred is a feeding regimen comprising a one time per day bolus feed with antioxidant, preferably with feeding medium containing antioxidant on each day of the culture run, from the beginning of the culture run to the day of harvesting the cells.

In accordance with the invention, the antioxidants of the invention can be fed to the cell culture at any of the aforementioned intervals in some way other than in the feed medium. As non-limiting examples, the antioxidants can be fed to the culture in DMSO, ethanol or water. As a non-limiting example, the culture may be fed with antioxidants and also fed with a feed medium, i.e., there may be more than one composition being fed.

As used herein, the term "feed" refers to any addition of any substance made to a culture after inoculation. Feeding can be one or more additions.

As used herein, the term "inoculation" refers to the addition of cells to starting medium to begin the culture.

As used herein, the terms "feed medium", "feed media" and "feeding medium" refer to a medium containing one or more nutrients that is added to the culture beginning at some time after inoculation.

As used herein, the term "basal medium" and "basal media" refers to starting medium to which cells are added to begin the culture.

In another of its embodiments, the present invention encompasses a cell culture method or process of increasing protein titer in a cell culture, comprising the addition of catechin to the culturing medium. A related embodiment involves a cell culture method in which catechin is supplied to the culture for the duration of the production run, and preferably is present in the feeding medium. A preferred embodiment relates to processes of culturing cells comprising a daily feeding of the culture with medium containing catechin. The addition of catechin to the cells in culture as provided by this method, preferably supplied more than one time during the culture run, more preferably, on a daily basis, increases, maintains viable cell density in the culture, allowing the cells to continue to produce protein, thereby maximizing protein production. Another related embodiment involves a cell culture method in which catechin is supplied to the culture in the basal media. The addition of catechin to the cells in the basal media as provided by this method increases and/or maintains viable cell density in the culture, allowing the cells to continue to produce protein, thereby maximizing protein production. Another related embodiment involves a cell culture method in which catechin is supplied to the culture in the basal media as well as for the duration of the production run, preferably in the feeding medium. A preferred embodiment relates to processes of culturing cells comprising cell inoculation in an antioxidant supplemented basal media and a daily feeding of the culture with medium containing catechin. The addition of catechin to the cells in culture as provided by this method increases and/or maintains viable cell density in the culture, allowing the cells to continue to produce protein, thereby maximizing protein production In another of its embodiments, the present invention encompasses a cell culture method or process of increasing protein titer in a cell culture, comprising the addition of rosmarinic acid to the culturing medium. A related embodiment involves a cell culture method in which rosmarinic acid is supplied to the culture for the duration of the production run, and preferably is present in the feeding medium. A preferred embodiment relates to processes of culturing cells comprising a daily feeding of the culture with medium containing rosmarinic acid. The addition of rosmarinic acid to the cells in culture as provided by this method, preferably supplied more than one time during the culture run, more preferably, on a daily basis, increases, maintains viable cell density in the culture, allowing the cells to continue to produce protein, thereby maximizing protein production. Another related embodiment involves a cell culture method in which rosmarinic acid is supplied to the culture in the basal media. The addition of rosmarinic acid to the cells in basal media as provided by this method increases and/or maintains viable cell density in the culture, allowing the cells to continue to produce protein, thereby maximizing protein production. Another related embodiment involves a cell culture method in which rosmarinic acid is supplied to the culture in the basal media as well as for the duration of the production run, preferably in the feeding medium. A preferred embodiment relates to processes of culturing cells comprising cell inoculation in an antioxidant supplemented basal media and a daily feeding of the culture with medium containing rosmarinic acid. The addition of rosmarinic acid to the cells in culture as provided by this method increases and/or maintains viable cell density in the culture, allowing the cells to continue to produce protein, thereby maximizing protein production.

In accordance with this invention, viable cell density is increased about 10-100% when the cell culture is supplemented with antioxidants, as compared with cell cultures in the absence of antioxidant supplementation.

In accordance with this invention, protein titer is increased, on average, about 30-130% when cell cultures are supplemented with antioxidants, as compared with cell cultures in the absence of antioxidant supplementation.

Screening Natural Phenolic Antioxidants for Bioproduction

Following the cell culture process described in Example 1, thirteen novel antioxidants (Table 1) were added to the feed media utilized in aCD137 cell culture. Three antioxidant concentrations were evaluated: 1 mM (Run #1-13), 0.25 mM (Run #17-29), and 0.0625 mM (Run #33-45). The antioxidants were dissolved in either pure ethanol or dimethyl sulfoxide (DMSO) at 50 mM stock concentration and added to feed media M154A1B at the designed final concentrations. The corresponding solvent negative controls were run number 16, 32, and 48. Two traditional antioxidants, ascorbic acid (Run #14, 30, and 46) and reduced glutathione (Run #15, 31, and 47), served as positive controls. The basal media M171B was not supplemented with antioxidant.

TABLE 1

List of Antioxidants and Concentrations Evaluated

| Run# | Component | Concentration (mM) |
|---|---|---|
| 1 | Catechin | 1 |
| 2 | Apigenin | 1 |
| 3 | Naringenin | 1 |
| 4 | Hesperetin | 1 |
| 5 | Quercetin | 1 |
| 6 | Pelargonidin | 1 |
| 7 | Genistein | 1 |
| 8 | Daidzein | 1 |
| 9 | Resveratrol | 1 |
| 10 | Melatonin | 1 |
| 11 | Chlorogenic acid | 1 |
| 12 | Rosmarinic acid | 1 |
| 13 | Silibinin | 1 |
| 14 | Ascorbic Acid | 1 |
| 15 | L-Glutathione reduced | 1 |
| 16 | Solvent-DMSO | 1% v/v |

TABLE 1-continued

List of Antioxidants and Concentrations Evaluated

| Run# | Component | Concentration (mM) |
|---|---|---|
| 17 | Catechin | 0.25 |
| 18 | Apigenin | 0.25 |
| 19 | Naringenin | 0.25 |
| 20 | Hesperetin | 0.25 |
| 21 | Quercetin | 0.25 |
| 22 | Pelargonidin | 0.25 |
| 23 | Genistein | 0.25 |
| 24 | Daidzein | 0.25 |
| 25 | Resveratrol | 0.25 |
| 26 | Melatonin | 0.25 |
| 27 | Chlorogenic acid | 0.25 |
| 28 | Rosmarinic acid | 0.25 |
| 29 | Silibinin | 0.25 |
| 30 | Ascorbic Acid | 0.25 |
| 31 | L-Glutathione reduced | 0.25 |
| 32 | Solvent-Ethanol | 1% v/v |
| 33 | Catechin | 0.0625 |
| 34 | Apigenin | 0.0625 |
| 35 | Naringenin | 0.0625 |
| 36 | Hesperetin | 0.0625 |
| 37 | Quercetin | 0.0625 |
| 38 | Pelargonidin | 0.0625 |
| 39 | Genistein | 0.0625 |
| 40 | Daidzein | 0.0625 |
| 41 | Resveratrol | 0.0625 |
| 42 | Melatonin | 0.0625 |
| 43 | Chlorogenic acid | 0.0625 |
| 44 | Rosmarinic acid | 0.0625 |
| 45 | Silibinin | 0.0625 |
| 46 | Ascorbic Acid | 0.0625 |
| 47 | L-Glutathione reduced | 0.0625 |
| 48 | Solvent-$H_2O$ | N/A |

As shown in FIG. 1, addition of the antioxidants to the feed media affected viable cell density (VCD) on day 8 (peak VCD). In some instances, viable cell density was increased by as much as 30% by the addition of antioxidant compared to the controls (DMSO, ethanol, or water).

Figure 2:
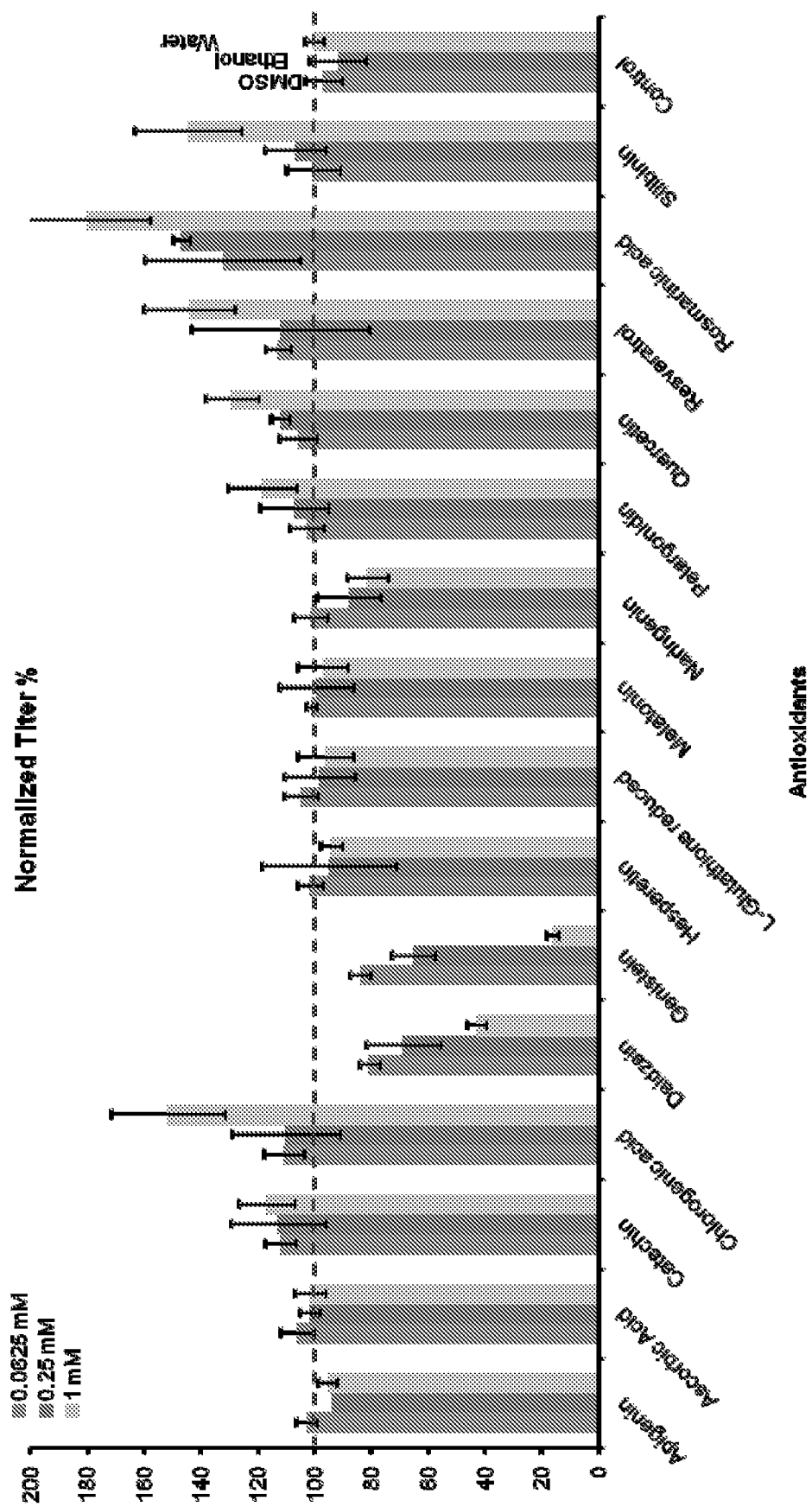
FIG. 2 shows the impact of 0.0625 mM, 0.25 mM and 1 mM of different antioxidants added to the feed media M154A1B on productivity of the cultured aCD137 cells. The basal media M17IB was not supplemented with antioxidant. The final titer (harvested on days 14) for each condition was normalized to the control condition with no additional antioxidants in the feed.

As shown in FIG. 2, addition of the antioxidants to the feed media also affected the productivity of the cultured cells. In some instances, protein titer was increased by as much as 80% by addition of antioxidant compared to the controls (DMSO, ethanol, or water).

The antioxidants with the greatest positive impact on protein titer are presented in Table 2 below. Addition of catechin, chlorogenic acid, resveratrol, and rosmarinic acid increased protein titer when feed at all three concentrations (0.0625-1 mM). Quercetin feed at 0.25 mM and 1 mM increased protein titer. Pelargonidin and silibinin feed increased protein titer when feed at 1 mM.

TABLE 2

List of Antioxidants and Concentrations that Improved Protein Titer

| Component | VCD % | Titer % | Concentration (mM) |
|---|---|---|---|
| Catechin | 102.01 | 116.67 | 1 |
| Catechin | 93.52 | 112.70 | 0.25 |
| Catechin | 98.66 | 111.90 | 0.0625 |
| Chlorogenic acid | 129.57 | 151.59 | 1 |
| Chlorogenic acid | 109.35 | 109.92 | 0.25 |
| Chlorogenic acid | 115.85 | 110.71 | 0.0625 |
| Pelargonidin | 104.47 | 118.25 | 1 |
| Quercetin | 123.11 | 128.97 | 1 |
| Quercetin | 119.28 | 111.90 | 0.25 |
| Resveratrol | 107.48 | 144.05 | 1 |

TABLE 2-continued

List of Antioxidants and Concentrations that Improved Protein Titer

| Component | VCD % | Titer % | Concentration (mM) |
|---|---|---|---|
| Resveratrol | 92.24 | 111.90 | 0.25 |
| Resveratrol | 102.53 | 112.70 | 0.0625 |
| Rosmarinic acid | 124.08 | 180.16 | 1 |
| Rosmarinic acid | 125.43 | 146.83 | 0.25 |
| Rosmarinic acid | 129.25 | 132.14 | 0.0625 |
| Silibinin | 99.11 | 144.44 | 1 |

Cells, Proteins and Cell Culture

In the cell culture processes or methods of this invention, the cells can be maintained in a variety of cell culture media, i.e., basal culture media, as conventionally known in the art. For example, the methods are applicable for use with large volumes of cells maintained in cell culture medium, which can be supplemented with nutrients and the like. Typically, "cell culturing medium" (also called "culture medium") is a term that is understood by the practitioner in the art and is known to refer to a nutrient solution in which cells, preferably animal or mammalian cells, are grown and which generally provides at least one or more components from the following: an energy source (usually in the form of a carbohydrate such as glucose); all essential amino acids, and generally the twenty basic amino acids, plus cysteine; vitamins and/or other organic compounds typically required at low concentrations; lipids or free fatty acids, e.g., linoleic acid; and trace elements, e.g., inorganic compounds or naturally occurring elements that are typically required at very low concentrations, usually in the micromolar range. Cell culture medium can also be supplemented to contain a variety of optional components, such as hormones and other growth factors, e.g., insulin, transferrin, epidermal growth factor, serum, and the like; salts, e.g., calcium, magnesium and phosphate, and buffers, e.g., HEPES; nucleosides and bases, e.g., adenosine, thymidine, hypoxanthine; and protein and tissue hydrolysates, e.g., hydrolyzed animal protein (peptone or peptone mixtures, which can be obtained from animal byproducts, purified gelatin or plant material); antibiotics, e.g., gentamycin; and cell protective agents, e.g., a PLURONIC® polyol (PLURONIC® F68). Preferred is a cell nutrition medium that is serum-free and free of products or ingredients of animal origin.

As is appreciated by the practitioner, animal or mammalian cells are cultured in a medium suitable for the particular cells being cultured and which can be determined by the person of skill in the art without undue experimentation. Commercially available media can be utilized and include, for example, Minimal Essential Medium (MEM, Sigma, St. Louis, Mo.); Ham's F10 Medium (Sigma); Dulbecco's Modified Eagles Medium (DMEM, Sigma); RPMI-1640 Medium (Sigma); HYCLONE® cell culture medium (HyClone, Logan, Utah); and chemically-defined (CD) media, which are formulated for particular cell types. To the foregoing, exemplary media can be added the above-described supplementary components or ingredients, including optional components, in appropriate concentrations or amounts, as necessary or desired, and as would be known and practiced by those having in the art using routine skill.

In addition, cell culture conditions suitable for the methods of the present invention are those that are typically employed and known for batch, fed-batch, or continuous culturing of cells, with attention paid to pH (e.g., about 6.5 to about 7.5), dissolved oxygen ($O_2$) (e.g., between about 5-90% of air saturation), carbon dioxide ($CO_2$) (e.g., between about 10-150%), agitation (between about 50 to 200 rpm) and humidity, in addition to temperature (between about 30° C. to 37° C.). As an illustrative, yet nonlimiting, example, a suitable cell culturing medium for the fed-batch processes of the present invention comprises a chemically defined basal and feed medium, preferably one or both containing the antioxidants of the invention (e.g., Example 1).

Animal cells, mammalian cells, cultured cells, animal or mammalian host cells, host cells, recombinant cells, recombinant host cells, and the like, are all terms for the cells that can be cultured according to the processes of this invention. Such cells are typically cell lines obtained or derived from mammals and are able to grow and survive when placed in either monolayer culture or suspension culture in medium containing appropriate nutrients and/or growth factors. Growth factors and nutrients that are necessary for the growth and maintenance of particular cell cultures are able to be readily determined empirically by those having skill in the pertinent art, such as is described, for example, by Barnes et al. (*Cell*, 22:649 (1980)); in Mather, J. P., ed., *Mammalian Cell Culture*, Plenum Press, NY (1984); and in U.S. Pat. No. 5,721,121.

Numerous types of cells can be cultured according to the methods of the present invention. The cells are typically animal or mammalian cells that can express and secrete, or that can be molecularly engineered to express and secrete, large quantities of a particular protein into the culture medium. It will be understood that the protein produced by a host cell can be endogenous or homologous to the host cell. Alternatively, and preferably, the protein is heterologous, i.e., foreign, to the host cell, for example, a human protein produced and secreted by a Chinese hamster ovary (CHO) host cell.

Examples of mammalian proteins that can be advantageously produced by the methods of this invention include, without limitation, cytokines, cytokine receptors, growth factors (e.g., EGF, HER-2, FGF-α, FGF-β, TGF-α, TGF-β, PDGF. IGF-1, IGF-2, NGF, NGF-β); growth factor receptors, including fusion or chimeric proteins. Other nonlimiting examples include growth hormones (e.g., human growth hormone, bovine growth hormone); insulin (e.g., insulin A chain and insulin B chain), proinsulin; erythropoietin (EPO); colony stimulating factors (e.g., G-CSF, GM-CSF, M-CSF); interleukins (e.g., IL-1 through IL-12); vascular endothelial growth factor (VEGF) and its receptor (VEGF-R); interferons (e.g., IFN-α, β, or γ); tumor necrosis factor (e.g., TNF-α and TNF-β) and their receptors, TNFR-1 and TNFR-2; thrombopoietin (TPO); thrombin; brain natriuretic peptide (BNP); clotting factors (e.g., Factor VIII, Factor IX, von Willebrands factor, and the like); anti-clotting factors; tissue plasminogen activator (TPA), e.g., urokinase or human urine or tissue type TPA; follicle stimulating hormone (FSH); luteinizing hormone (LH); calcitonin; CD proteins (e.g., CD3, CD4, CD8, CD28, CD19, etc.); CTLA proteins (e.g., CTLA4); T-cell and B-cell receptor proteins; bone morphogenic proteins (BNPs, e.g., BMP-1, BMP-2, BMP-3, etc.); neurotrophic factors, e.g., bone derived neurotrophic factor (BDNF); neurotrophins, e.g., 3-6; renin; rheumatoid factor; RANTES; albumin; relaxin; macrophage inhibitory protein (e.g., MIP-1, MIP-2); viral proteins or antigens; surface membrane proteins; ion channel proteins; enzymes; regulatory proteins; antibodies; immunomodulatory proteins, (e.g., HLA, MHC, the B7 family); homing receptors; transport proteins; superoxide dismutase (SOD); G-protein coupled receptor proteins (GPCRs); neuromodulatory proteins; Alzheimer's Disease associated proteins and peptides, (e.g., A-beta), and others as known in the art. Fusion proteins and polypeptides, chimeric proteins and polypeptides, as well as fragments or portions, or mutants, variants, or analogs of any of the aforementioned proteins and polypeptides are also included among the suitable proteins, polypeptides and peptides that can be produced by the methods of the present invention.

Nonlimiting examples of animal or mammalian host cells suitable for harboring, expressing, and producing proteins for subsequent isolation and/or purification include Chinese hamster ovary cells (CHO), such as CHO-K1 (ATCC® CCL-61), DG44 (Chasin et al., *Som. Cell Molec. Genet.*, 12:555-556 (1986); Kolkekar et al., *Biochemistry*, 36:10901-10909 (1997); and WO 01/92337 A2), dihydrofolate reductase negative CHO cells (CHO/-DHFR, Urlaub et al., *Proc. Natl. Acad. Sci. USA*, 77:4216 (1980)), and dp12.CHO cells (U.S. Pat. No. 5,721,121); monkey kidney CV1 cells transformed by SV40 (COS cells, COS-7, ATCC® CRL-1651); human embryonic kidney cells (e.g., 293 cells, or 293 cells subcloned for growth in suspension culture, Graham et al., *J. Gen. Virol.*, 36:59 (1977)); baby hamster kidney cells (BHK, ATCC® CCL-10); monkey kidney cells (CV1, ATCC® CCL-70); African green monkey kidney cells (VERO-76, ATCC® CRL-1587; VERO, ATCC® CCL-81); mouse sertoli cells (TM4, Mather, *Biol. Reprod.*, 23:243-251 (1980)); human cervical carcinoma cells (HELA, ATCC® CCL-2); canine kidney cells (MDCK, ATCC® CCL-34); human lung cells (W138, ATCC® CCL-75); human hepatoma cells (HEP-G2, HB 8065); mouse mammary tumor cells (MMT 060562, ATCC® CCL-51); buffalo rat liver cells (BRL 3A, ATCC® CRL-1442); TRI cells (Mather, *Annals NY Acad. Sci.*, 383:44-68 (1982)); MCR 5 cells; FS4 cells. Preferred are CHO cells, particularly, CHO/-DHFR cells.

The cells suitable for culturing in the methods and processes of the present invention can contain introduced (e.g., via transformation, transfection, infection, or injection) expression vectors (constructs), such as plasmids and the like, that harbor coding sequences, or portions thereof, encoding the proteins for expression and production in the culturing process. Such expression vectors contain the necessary elements for the transcription and translation of the inserted coding sequence. Methods which are well known to and practiced by those skilled in the art can be used to construct expression vectors containing sequences encoding the produced proteins and polypeptides, as well as the appropriate transcriptional and translational control elements. These methods include in vitro recombinant DNA techniques, synthetic techniques, and in vivo genetic recombination. Such techniques are described in Sambrook, J. et al., *Molecular Cloning, A Laboratory Manual*, Cold Spring Harbor Press, Plainview, N.Y. (1989) and in Ausubel, F. M. et al., *Current Protocols in Molecular Biology*, John Wiley & Sons, New York, N.Y. (1989).

Control elements, or regulatory sequences, are those non-translated regions of the vector (e.g., enhancers, promoters, 5' and 3' untranslated regions) that interact with host cellular proteins to carry out transcription and translation. Such elements can vary in their strength and specificity. Depending on the vector system and host cell utilized, any number of suitable transcription and translation elements, including constitutive and inducible promoters, can be used. In mammalian cell systems, promoters from mammalian genes or from mammalian viruses are preferred. The constructs for use in protein expression systems are designed to contain at least one promoter, an enhancer sequence (optional, for mammalian expression systems), and other sequences as necessary or required for proper transcription and regulation of gene expression (e.g., transcriptional initiation and termination sequences, origin of replication sites, polyadenylation sequences, e.g., the Bovine Growth Hormone (BGH) poly A sequence).

As will be appreciated by those skilled in the art, the selection of the appropriate vector, components for proper transcription, expression, and isolation of proteins produced in eukaryotic expression systems is known and routinely determined and practiced by those having skill in the art. The expression of proteins by the cells cultured in accordance with the methods of this invention can be placed under the control of promoters such as viral promoters, e.g., cytomegalovirus (CMV), Rous sarcoma virus (RSV), phosphoglycerol kinase (PGK), thymidine kinase (TK), or the α-ACTIN® promoter. Further, regulated promoters confer inducibility by particular compounds or molecules, e.g., the glucocorticoid response element (GRE) of mouse mammary tumor virus (MMTV) is induced by glucocorticoids (Chandler, V. et al., *Cell*, 33:489-499 (1983)). Also, tissue-specific promoters or regulatory elements can be used (Swift, G. et al., *Cell*, 38:639-646 (1984)), if necessary or desired.

Expression constructs can be introduced into cells by a variety of gene transfer methods known to those skilled in the art, for example, conventional gene transfection methods, such as calcium phosphate co-precipitation, liposomal transfection, microinjection, electroporation, and infection or viral transduction. The choice of the method is within the competence of the skilled practitioner in the art. It will be apparent to those skilled in the art that one or more constructs carrying DNA sequences for expression in cells can be transfected into the cells such that expression products are subsequently produced in and/or obtained from the cells.

In a particular aspect, mammalian expression systems containing appropriate control and regulatory sequences are preferred for use in protein expressing mammalian cells of the present invention. Commonly used eukaryotic control sequences for generating mammalian expression vectors include promoters and control sequences compatible with mammalian cells such as, for example, the cytomegalovirus (CMV) promoter (CDM8 vector) and avian sarcoma virus (ASV) πLN vector. Other commonly used promoters include the early and late promoters from Simian Virus 40 (SV40) (Fiers et al., *Nature*, 273:113 (1973)), or other viral promoters such as those derived from polyoma, Adenovirus 2, and bovine papilloma virus. An inducible promoter, such as hMTII (Karin et al., *Nature*, 299:797-802 (1982)) can also be used.

Examples of expression vectors suitable for eukaryotic host cells include, but are not limited to, vectors for mammalian host cells (e.g., BPV-1, pHyg, pRSV, pSV2, pTK2 (Maniatis); pIRES (Clontech); pRc/CMV2, pRc/RSV, pSFV1 (Life Technologies); pVPakc Vectors, pCMV vectors, pSG5 vectors (Stratagene), retroviral vectors (e.g., pFB vectors (Stratagene)), pcDNA-3 (Invitrogen), adenoviral vectors; Adeno-associated virus vectors, baculovirus vectors, yeast vectors (e.g., pESC vectors (Stratagene)), or modified forms of any of the foregoing. Vectors can also contain enhancer sequences upstream or downstream of promoter region sequences for optimizing gene expression.

A selectable marker can also be used in a recombinant vector (e.g., a plasmid) to confer resistance to the cells harboring (preferably, having stably integrated) the vector to allow their selection in appropriate selection medium. A number of selection systems can be used, including but not limited to, the Herpes Simplex Virus thymidine kinase (HSV TK), (Wigler et al., *Cell*, 11:223 (1977)), hypoxanthineguanine phosphoribosyltransferase (HGPRT), (Szybalska et al., *Proc. Natl. Acad. Sci. USA*, 48:202 (1992)), and adenine phosphoribosyltransferase (Lowy et al., *Cell*, 22:817 (1980)) genes, which can be employed in tk-, hgprt-, or aprt-cells (APRT), respectively.

Anti-metabolite resistance can also be used as the basis of selection for the following nonlimiting examples of marker genes: dhfr, which confers resistance to methotrexate (Wigler et al., *Proc. Natl. Acad. Sci. USA*, 77:357 (1980); and O'Hare et al., *Proc. Natl. Acad. Sci. USA*, 78:1527 (1981)); gpt, which confers resistance to mycophenolic acid (Mulligan et al., *Proc. Natl. Acad. Sci. USA*, 78:2072 (1981)); neo, which confers resistance to the aminoglycoside G418 (Clin. Pharmacy, 12:488-505; Wu et al., *Biotherapy*, 3:87-95 (1991); Tolstoshev, *Ann. Rev. Pharmacol. Toxicol.*, 32:573-596 (1993); Mulligan, *Science*, 260:926-932 (1993); Anderson, *Ann. Rev. Biochem.*, 62:191-21 (1993); *TIB TECH*, 11(5):155-215 (May 1993); and hygro, which confers resistance to hygromycin (Santerre et al., *Gene*, 30:147 (1984)). Methods commonly known in the art of recombinant DNA technology can be routinely applied to select the desired recombinant cell clones, and such methods are described, for example, in Ausubel et al., eds., *Current Protocols in Molecular Biology*, John Wiley & Sons, NY (1993); Kriegler, *Gene Transfer and Expression, A Laboratory Manual*, Stockton Press, N.Y. (1990); in Dracopoli et al., eds., Chapters 12 and 13, *Current Protocols in Human Genetics*, John Wiley & Sons, NY (1994); Colberre-Garapin et al., *J. Mol. Biol.*, 150:1 (1981), which are incorporated by reference herein in their entireties.

In addition, the expression levels of an expressed protein molecule can be increased by vector amplification (for a review, see Bebbington et al., Chapter 8: "The use of vectors based on gene amplification for the expression of cloned genes in mammalian cells in DNA cloning", *DNA Cloning: A Practical Approach*, Vol. 3, pp. 163-188, IRL Press Limited (1987)). When a marker in the vector system expressing a protein is amplifiable, an increase in the level of inhibitor present in the host cell culture will increase the number of copies of the marker gene. Since the amplified region is associated with the protein-encoding gene, production of the protein will concomitantly increase (Crouse et al., *Mol. Cell. Biol.*, 3:257 (1983)).

Vectors which harbor glutamine synthase (GS) or dihydrofolate reductase (DHFR) encoding nucleic acid as the selectable markers can be amplified in the presence of the drugs methionine sulphoximine or methotrexate, respectively. An advantage of glutamine synthase based vectors is the availability of cell lines (e.g., the murine myeloma cell line, NS0) which are glutamine synthase negative. Glutamine synthase expression systems can also function in glutamine synthase expressing cells (e.g., CHO cells) by providing additional inhibitor to prevent the functioning of the endogenous gene.

Vectors that express DHFR as the selectable marker include, but are not limited to, the pSV2-dhfr plasmid (Subramani et al., *Mol. Cell. Biol.*, 1:854 (1981). Vectors that express glutamine synthase as the selectable marker include, but are not limited to, the pEE6 expression vector described in Stephens et al., *Nucl. Acids. Res.*, 17:7110 (1989). A glutamine synthase expression system and components thereof are detailed in PCT publications: WO 87/04462; WO 86/05807; WO 89/01036; WO 89/10404; and WO 91/06657 which are incorporated by reference herein in their entireties. In addition, glutamine synthase expression vectors that can be used in accordance with the present invention are commercially available from suppliers, including, for example, Lonza Biologics, Inc. (Portsmouth, N.H.).

Types of Cell Cultures

For the purposes of understanding, yet without limitation, it will be appreciated by the skilled practitioner that cell cultures and culturing runs for protein production can include three general types; namely, continuous culture, batch culture and fed-batch culture. In a continuous culture, for example, fresh culture medium supplement (i.e., feeding medium) is provided to the cells during the culturing period, while old culture medium is removed daily and the product is harvested, for example, daily or continuously. In continuous culture, feeding medium can be added daily and can be added continuously, i.e., as a drip or infusion. For continuous culturing, the cells can remain in culture as long as is desired, so long as the cells remain alive and the environmental and culturing conditions are maintained.

In batch culture, cells are initially cultured in medium and this medium is neither removed, replaced, nor supplemented, i.e., the cells are not "fed" with new medium, during or before the end of the culturing run. The desired product is harvested at the end of the culturing run.

For fed-batch cultures, the culturing run time is increased by supplementing the culture medium one or more times daily (or continuously) with fresh medium during the run, i.e., the cells are "fed" with new medium ("feeding medium") during the culturing period. Fed-batch cultures can include the various feeding regimens and times as described above, for example, daily, every other day, every two days, etc., more than once per day, or less than once per day, and so on. Further, fed-batch cultures can be fed continuously with feeding medium. The desired product is then harvested at the end of the culturing/production run.

Phases of Cell Culture and Associated Parameters

The term "inoculation" refers to the addition of cells to starting medium to begin the culture.

The growth phase of a culture is the phase during which the viable cell density at any time point is higher than at any previous time point.

The stationary phase of a culture is the phase during which the viable cell density is approximately constant (i.e., within measuring error) over a time period of any length.

The death phase of a culture is the phase that comes after the growth phase or after the growth phase and the stationary phase, and during which the viable cell density at any time point is lower than at any previous time point during that phase.

In a growth-associated culture process, the production phase may start during the extended growth phase.

In a non-growth associated culture process, the production phase of cell culture may be the stationary phase.

Preferably, the culture medium is supplemented ("fed") during the production phase to support continued protein production, particularly in an extended production phase, and to attain ample quantities of protein product. Feeding can occur on a daily basis, or according to other schedules to support cell viability and protein production.

Antioxidants Improved Process Performance for Multiple CHO Clones aCD137 Cells

In another embodiment, the dhfr-negative Chinese Hamster Ovary (CHO) cell line DG44 (Invitrogen Corp. Carlsbad, Calif.) were transfected in order to establish a stable cell line expressing a human IgG4 antibody.

The transfected CHO DG44 cells expressing the antibody was grown in the presence of antioxidants according to the methods of the invention.

As shown in FIG. 3, catechin, chlorogenic acid, quercetin, resveratrol or rosmarinic acid increased viable cell density and protein titer when added to both the basal media at 0.07 mM and the feed media at 1 mM.

Additionally, lactate production was reduced. Lactate produced in the glucose metabolism process is a major inhibitory waste product in mammalian cell cultures. High lactate concentrations may be an indication of malfunction of cell energy metabolism. Additionally, high concentrations of lactate may also alter the pH of the cell culture. Therefore, it is preferred to maintain a lower lactate level (<5 g/L) during the course of production.

Figure 4:
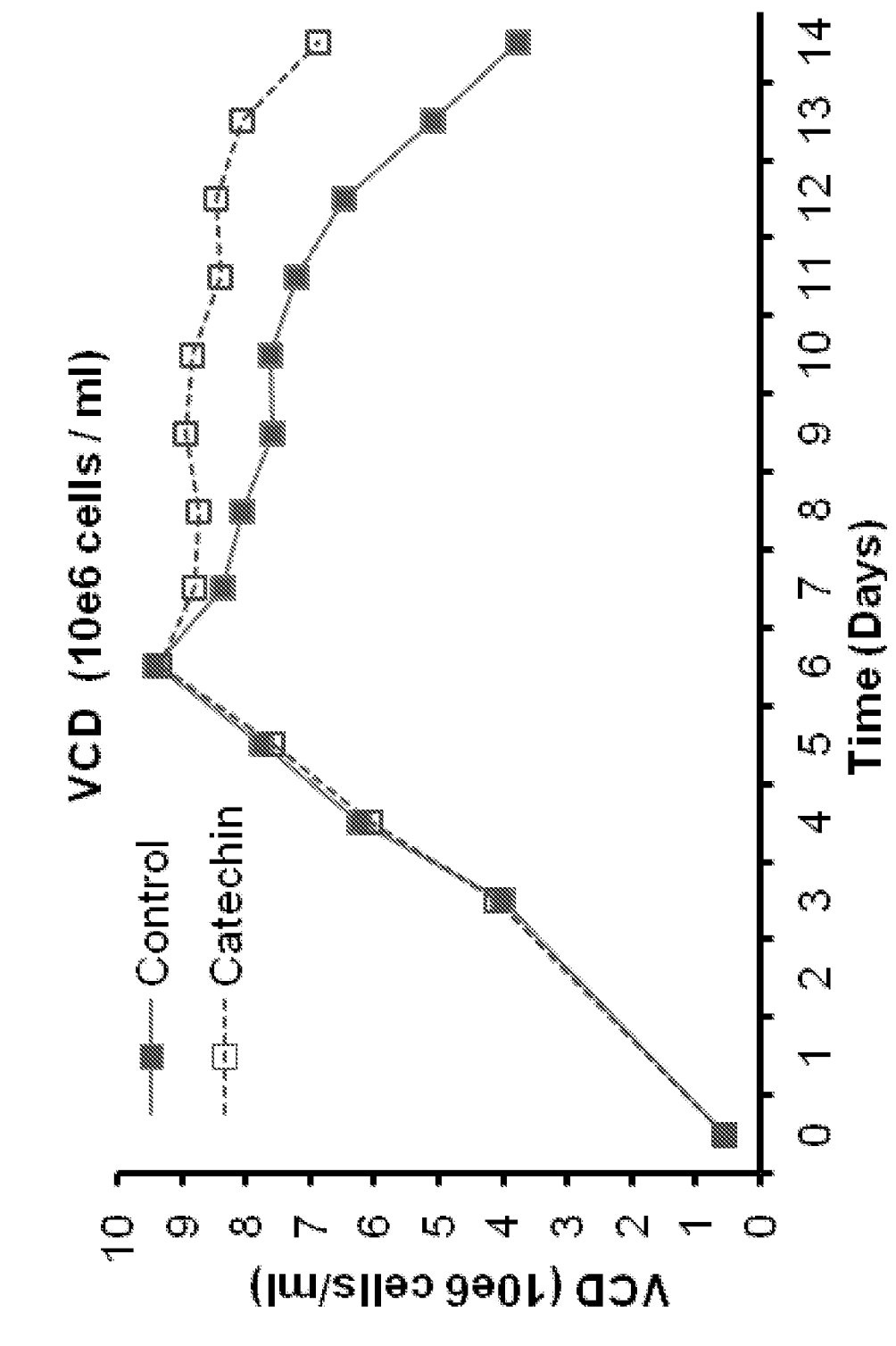
FIG. 4A-D show the impact of catechin(□) on aCD137 cell culture (A) viable cell density, (B) cell viability, (C) normalized protein titer, and (D) ammonium concentration. Catechin was added to feed media F3.2 at 1 mM. The media was then used in a standard shaker flask fed-batch culture with aCD137 cells together with basal media B1
Figure 4:
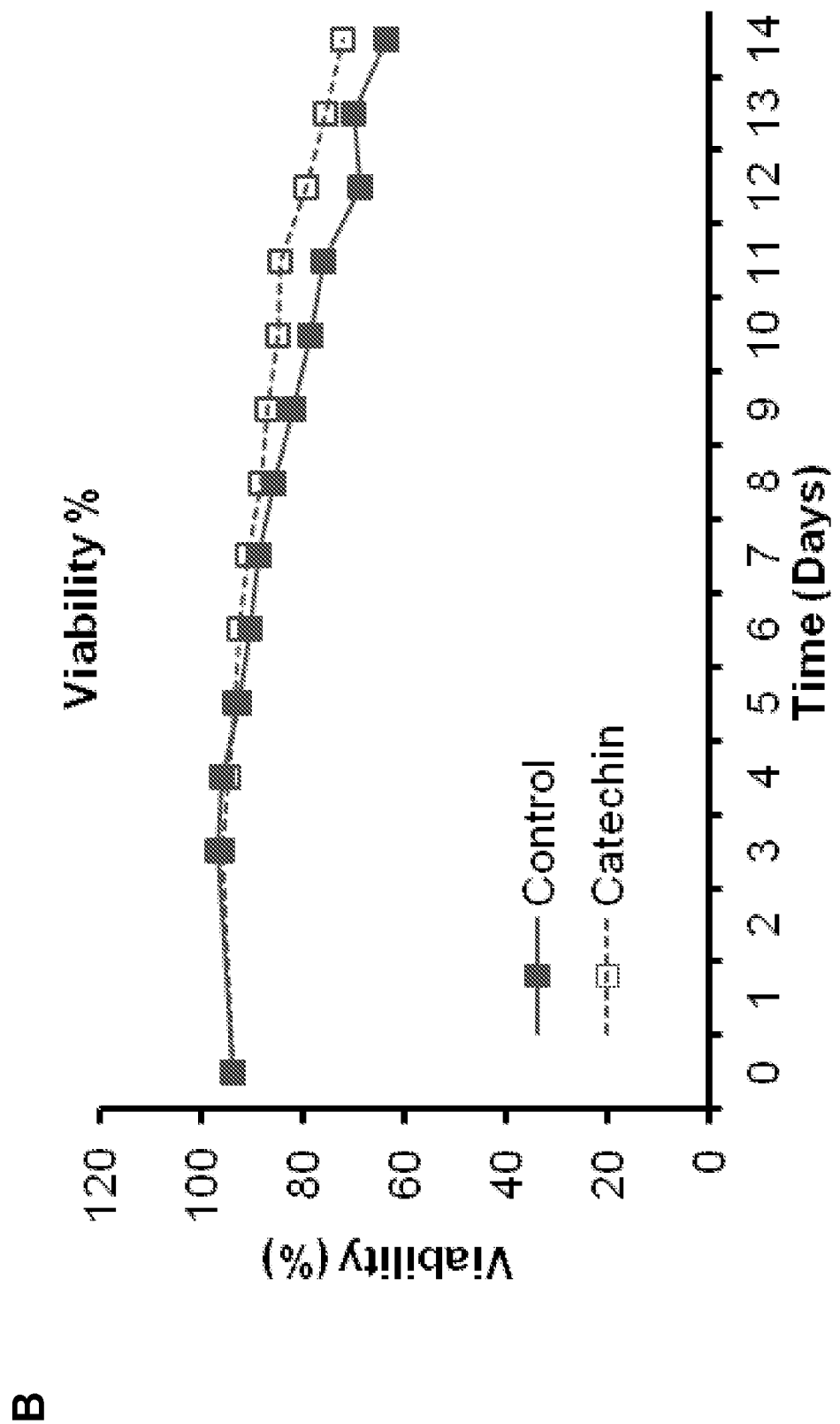
Figure 4:
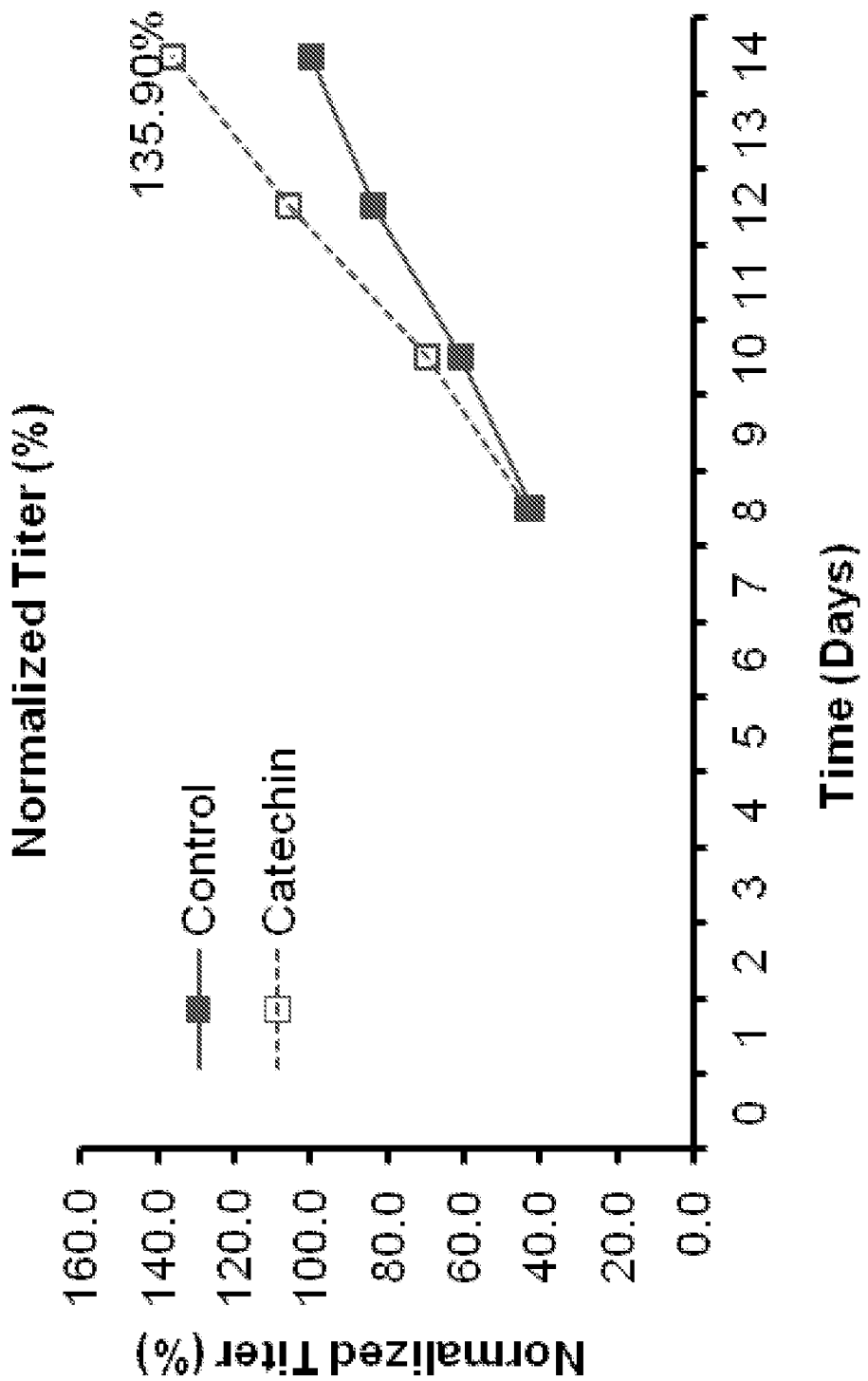
Figure 4:
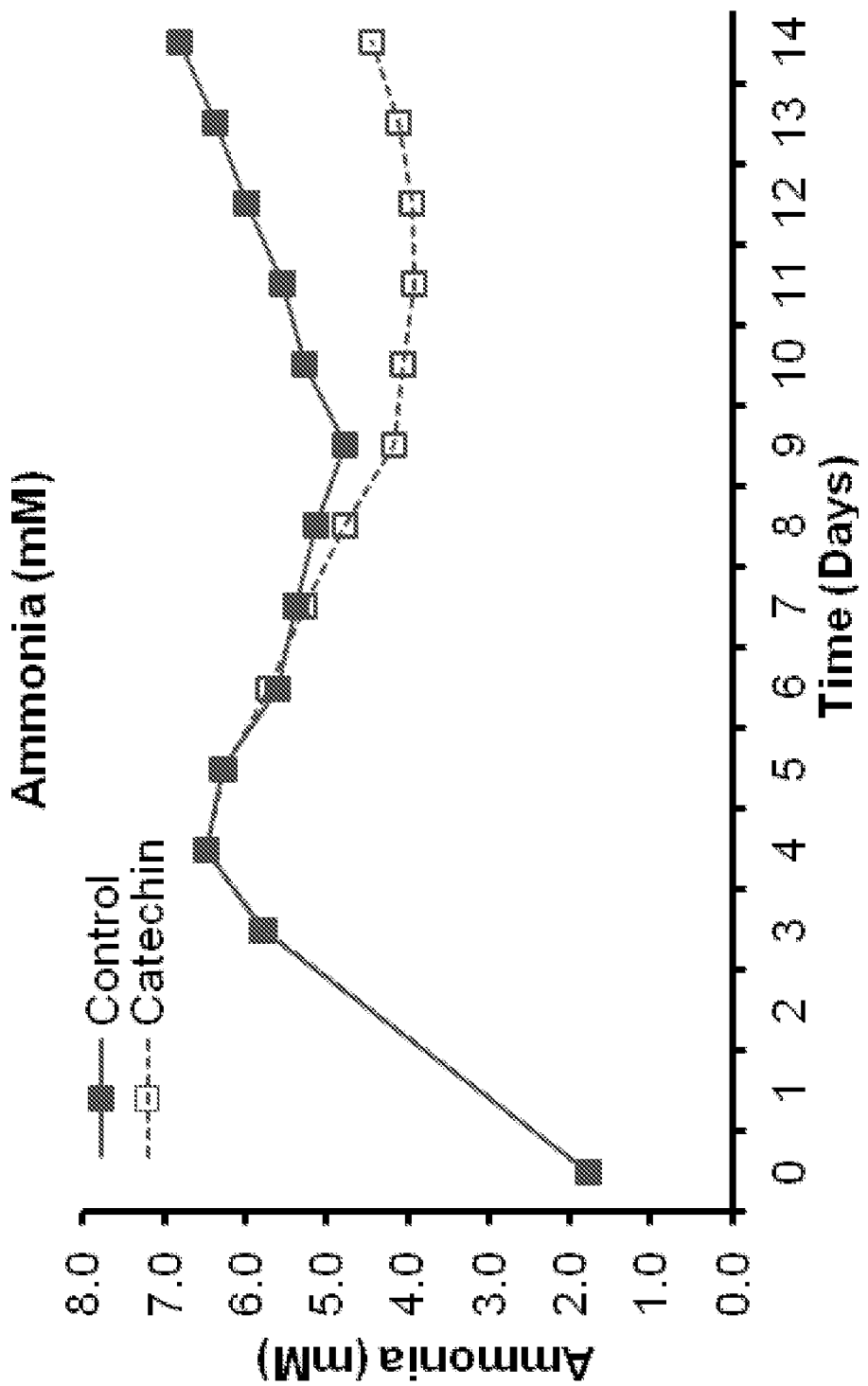

As shown in FIG. 4, catechin addition to the cell culture maintained viable cell density and increased protein titer when added to the feed media at 1 mM.

Further, ammonium formation was reduced. Like lactate, ammonium is a major inhibitory waste product in mammalian cell cultures. High ammonium concentrations may alter the pH of the cell culture. Additionally, it is believed that high ammonium level may alter the quality attributes of the glycoproteins produced (N-link, etc.). Therefore, it is preferred to maintain a lower ammonium level for a cell culture process (<10 mM; <5 mM mostly preferred).

Figure 5:
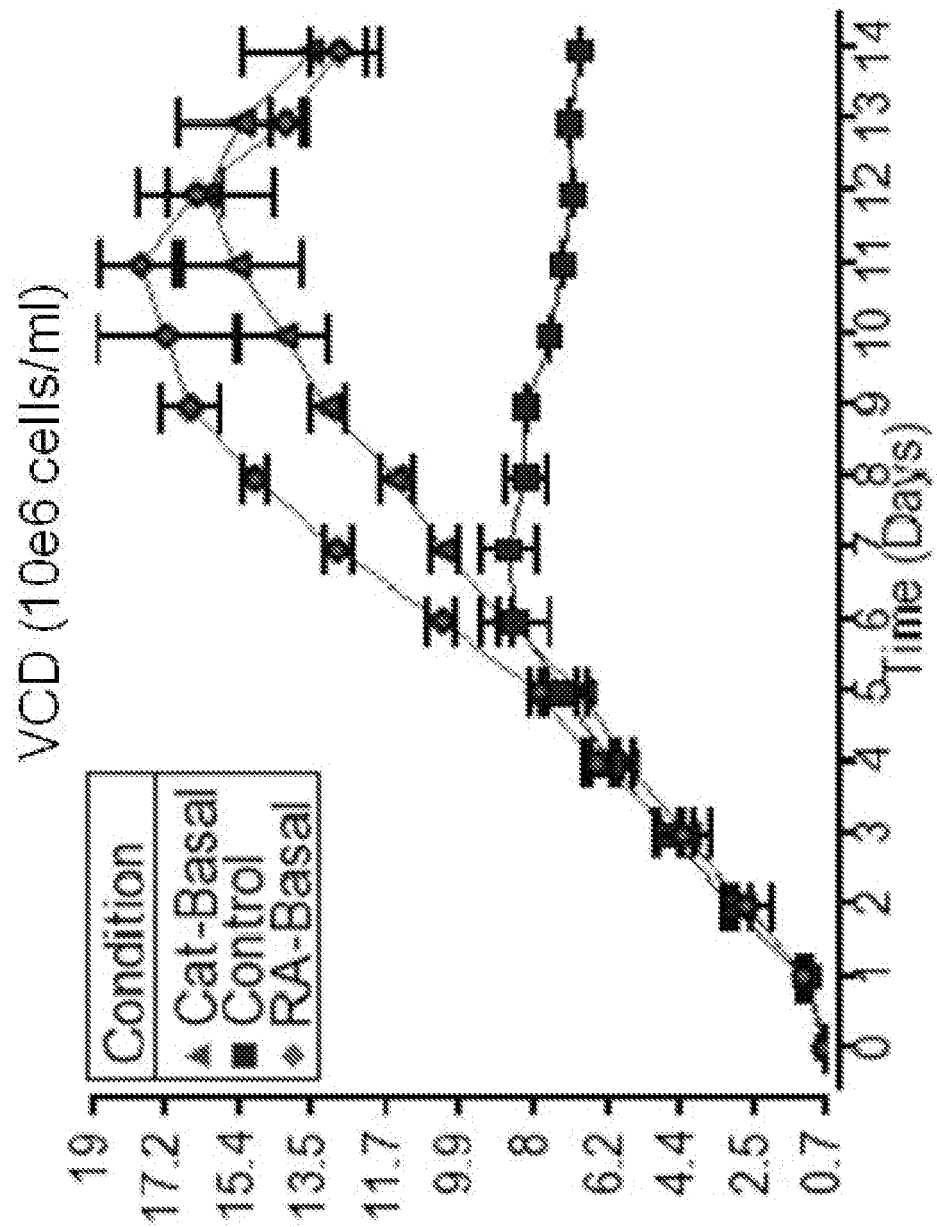
FIG. 5A-E shows the impact of rosmarinic acid(♦) and catechin(▲) on aCD137 cell culture (A) viable cell density, (B) cell viability, (C) normalized protein titer, (D) lactate concentration and (E) ammonium concentration. Rosmarinic acid or catechin were added to basal media M17IB at 0.1 mM. The media was then used in a standard 7-liter fed-batch culture together with feed media M154A1B.
Figure 5:
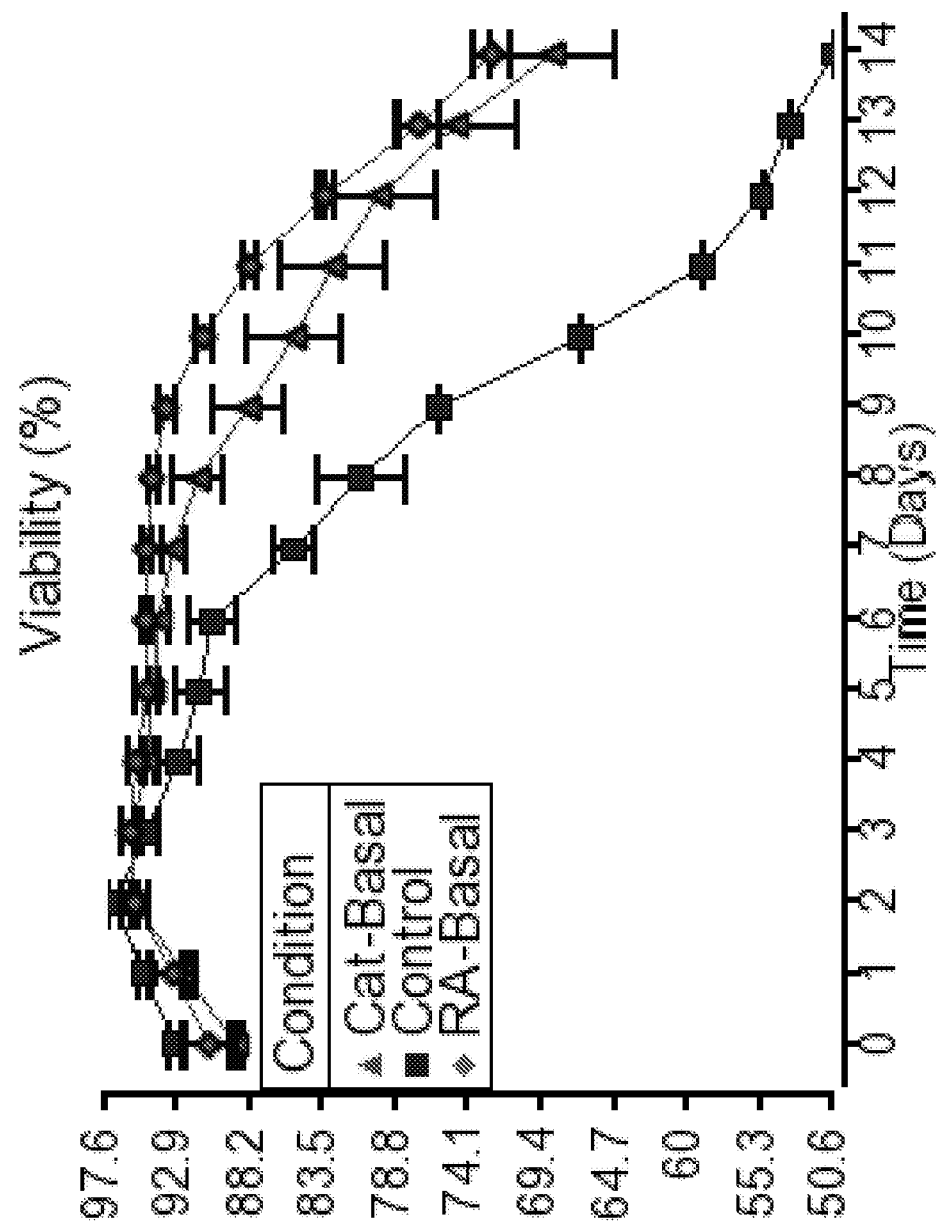
Figure 5:
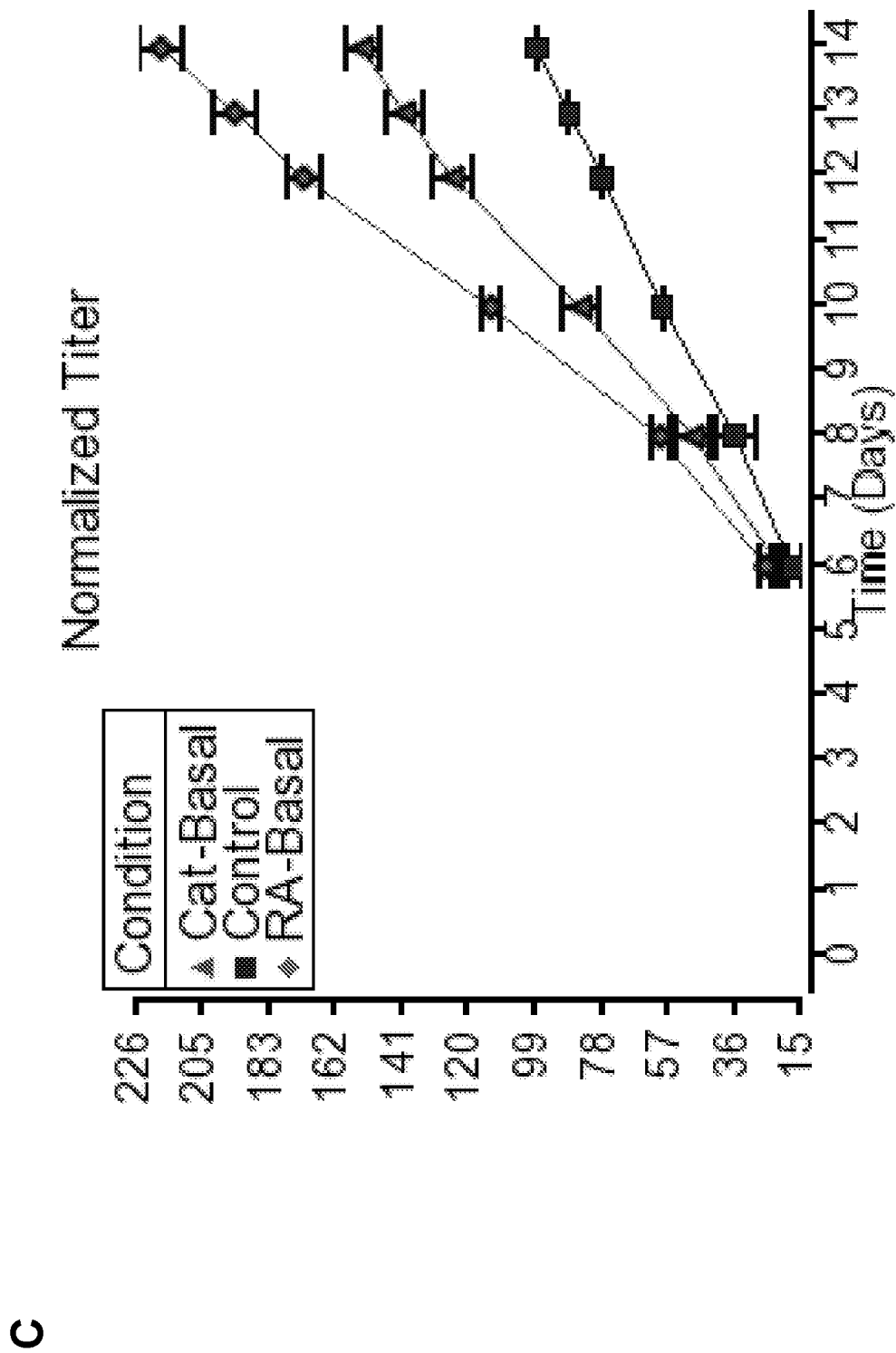
Figure 5:
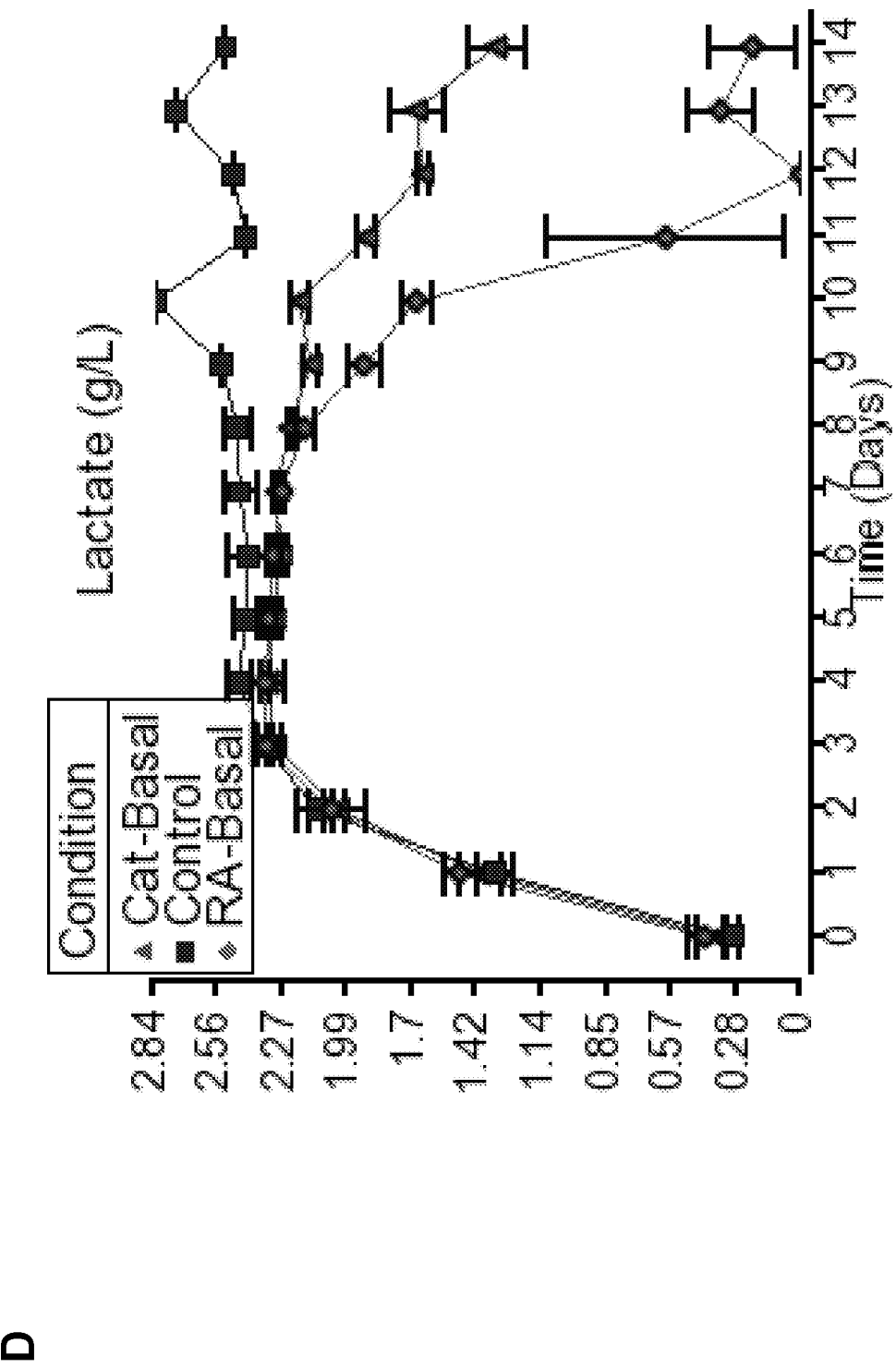
Figure 5:
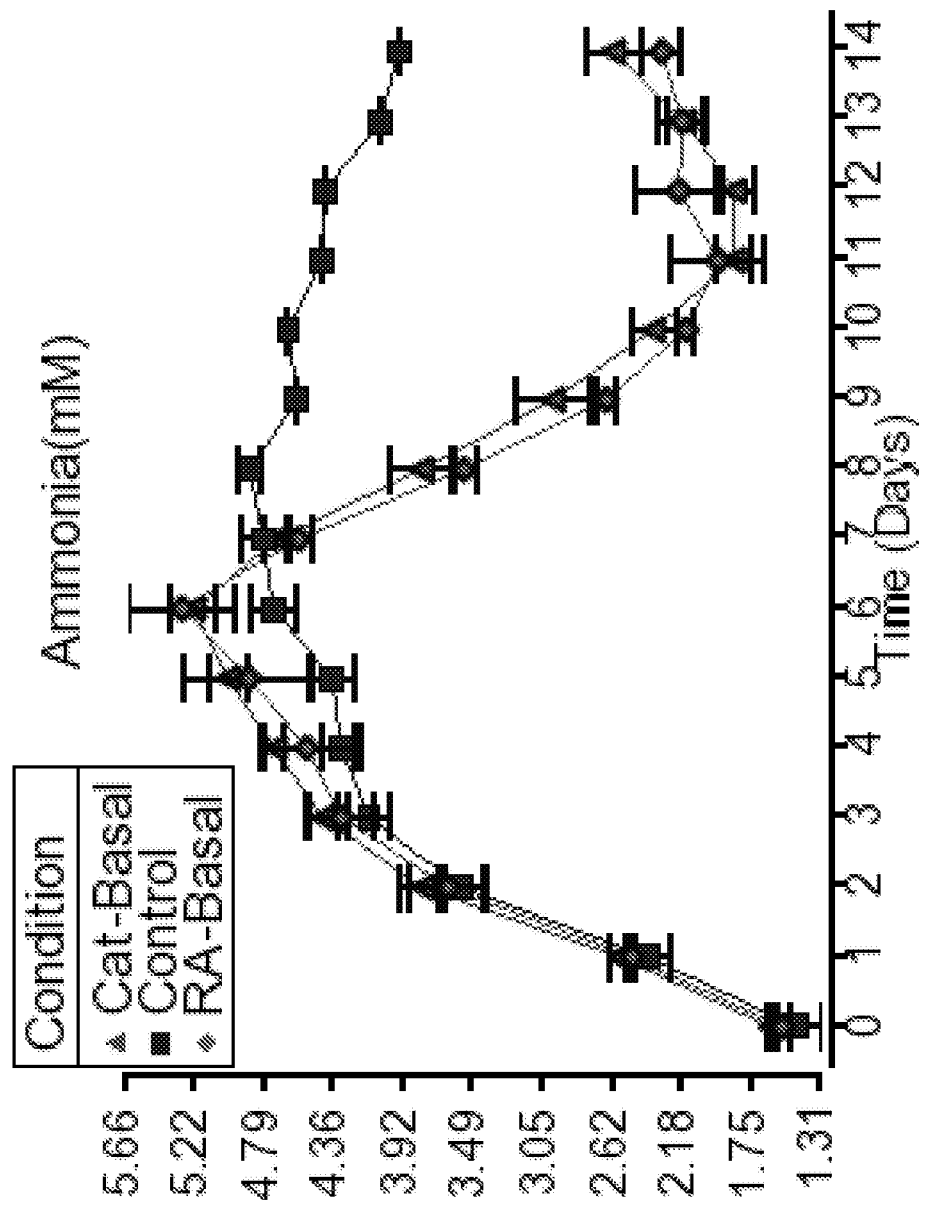

As shown in FIG. 5, rosmarinic acid or catechin addition to the cell culture increased viable cell density and protein titer; and reduced ammonium and lactate formation. Rosmarinic acid or catechin was added to basal media at 0.1 mM.

Figure 6:
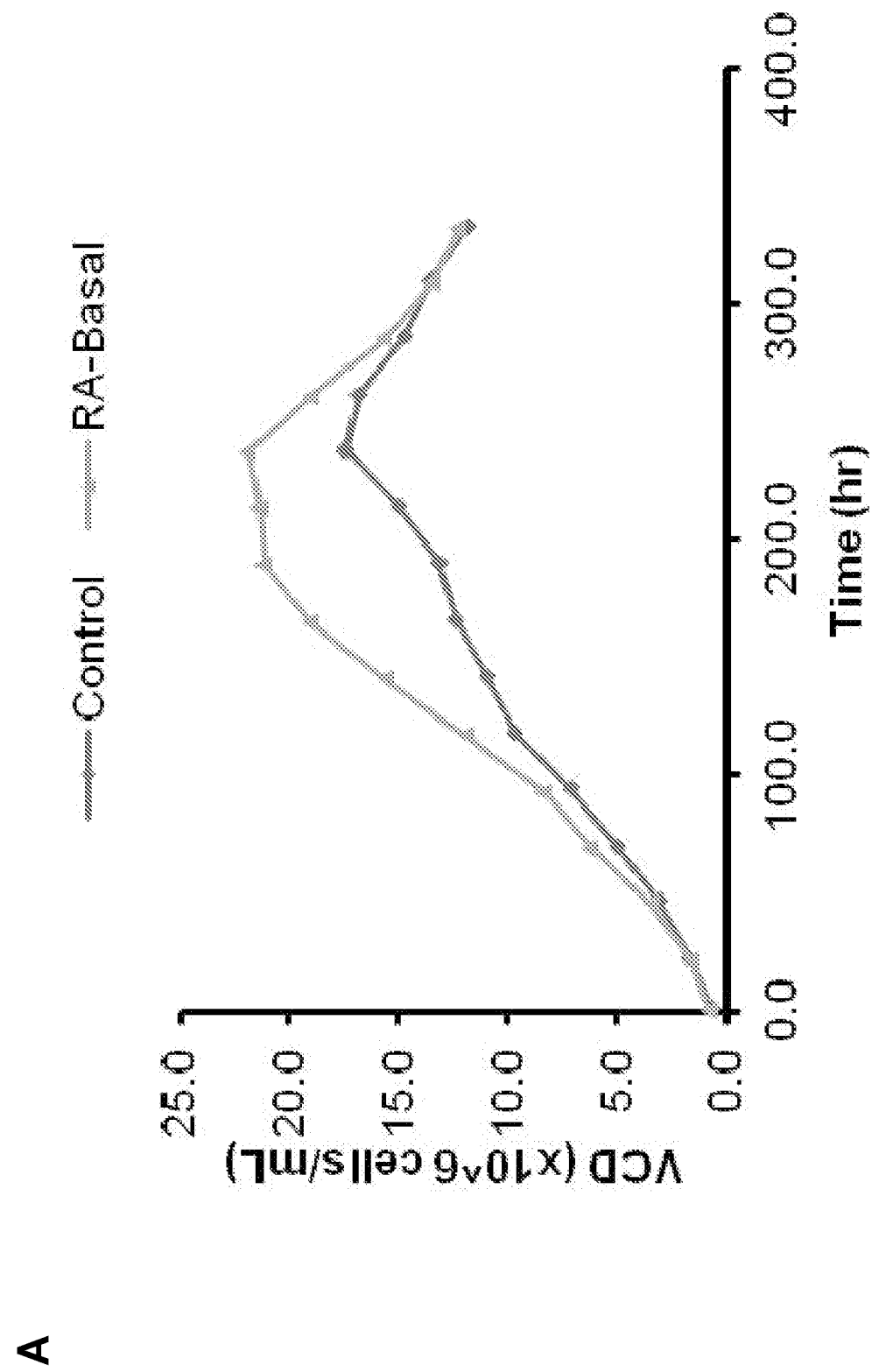
FIG. 6A-D shows the impact of rosmarinic acid (▲) on aCD137 cell culture (A) viable cell density, (B) cell viability, (C) normalized protein titer, and (D) lactate concentration. Rosmarinic acid was added to basal media M17IB at 0.1 mM. The media was then used in a standard fed-batch culture together with feed media M154A1B.
Figure 6:
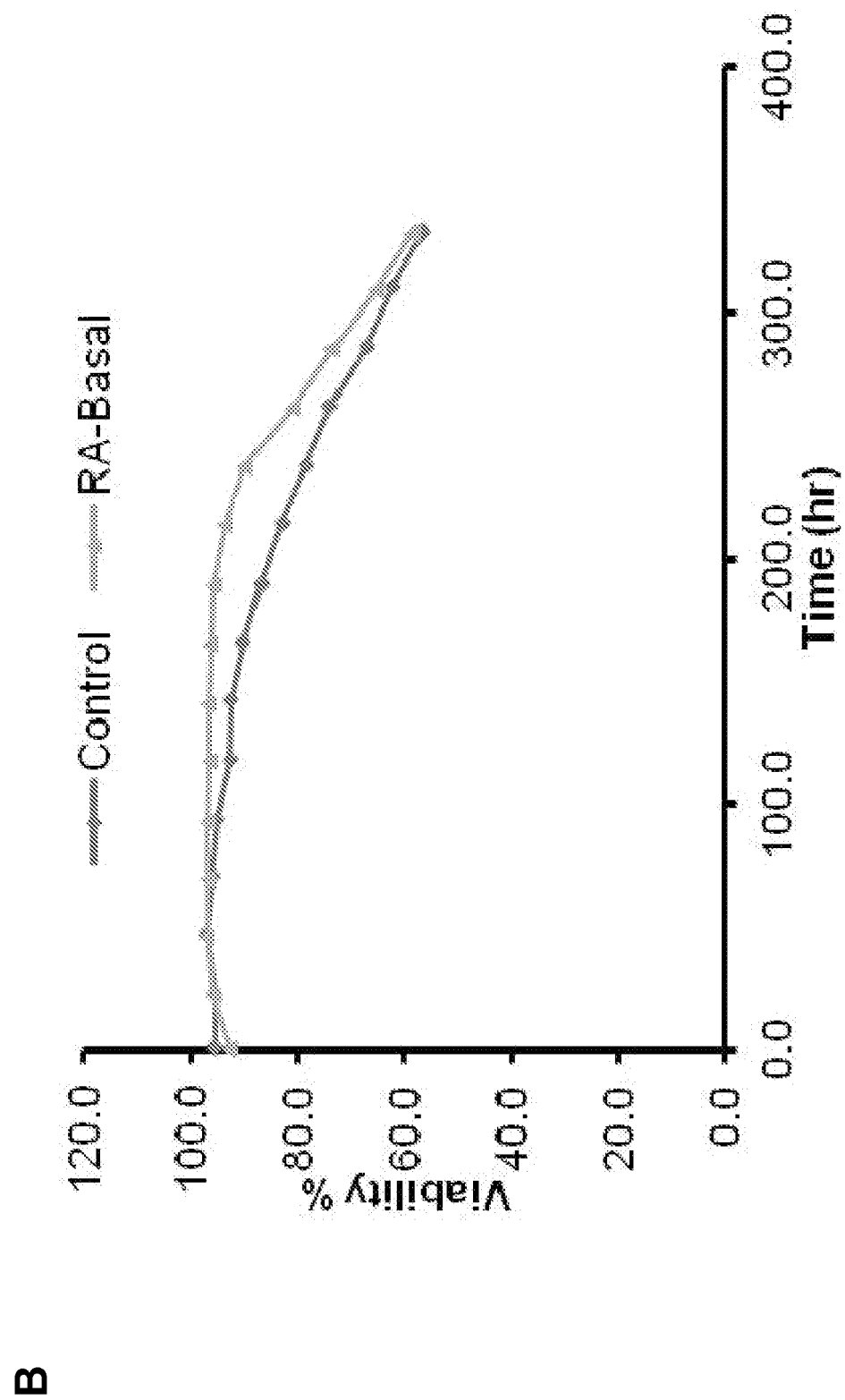
Figure 6:
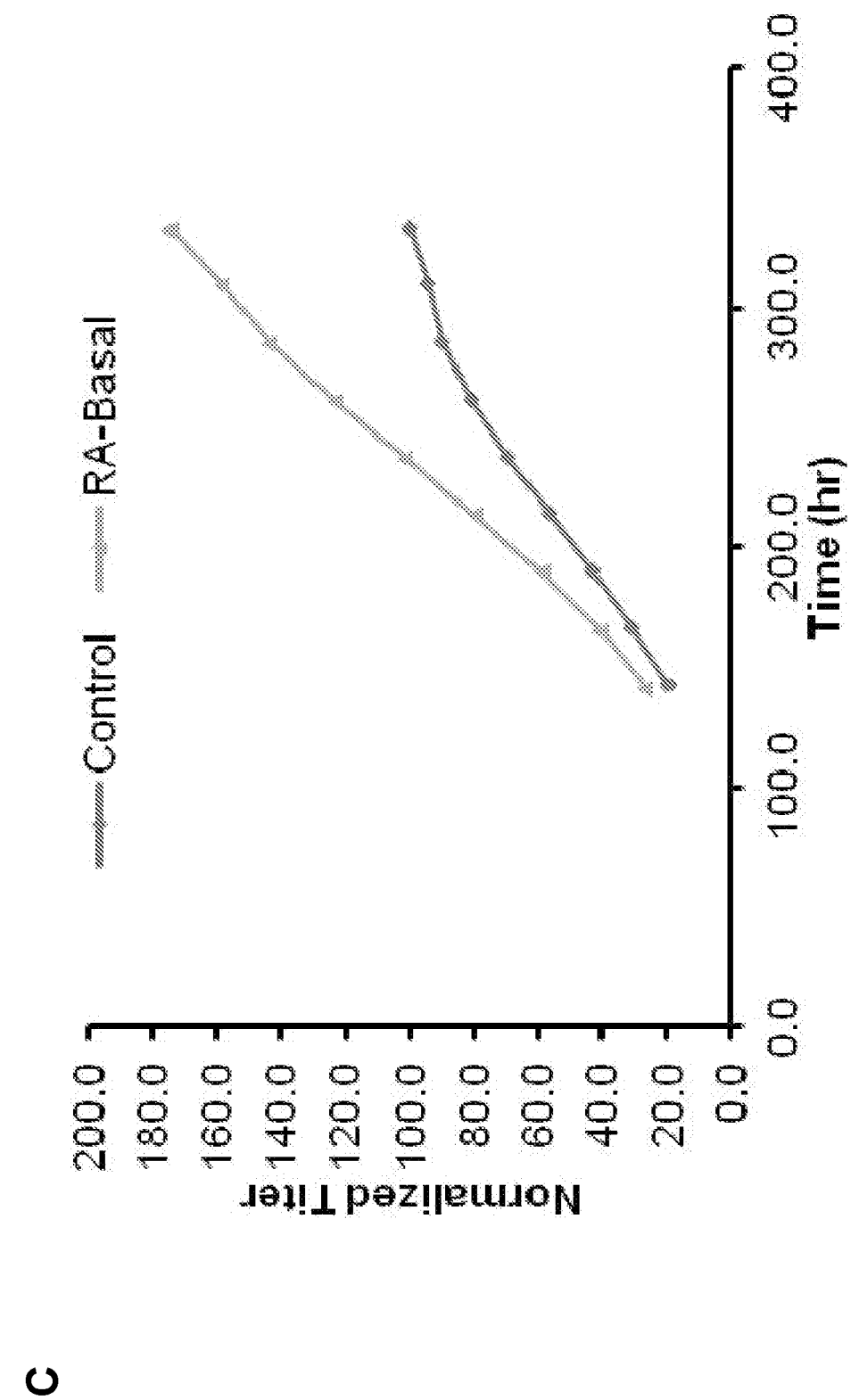
Figure 6:
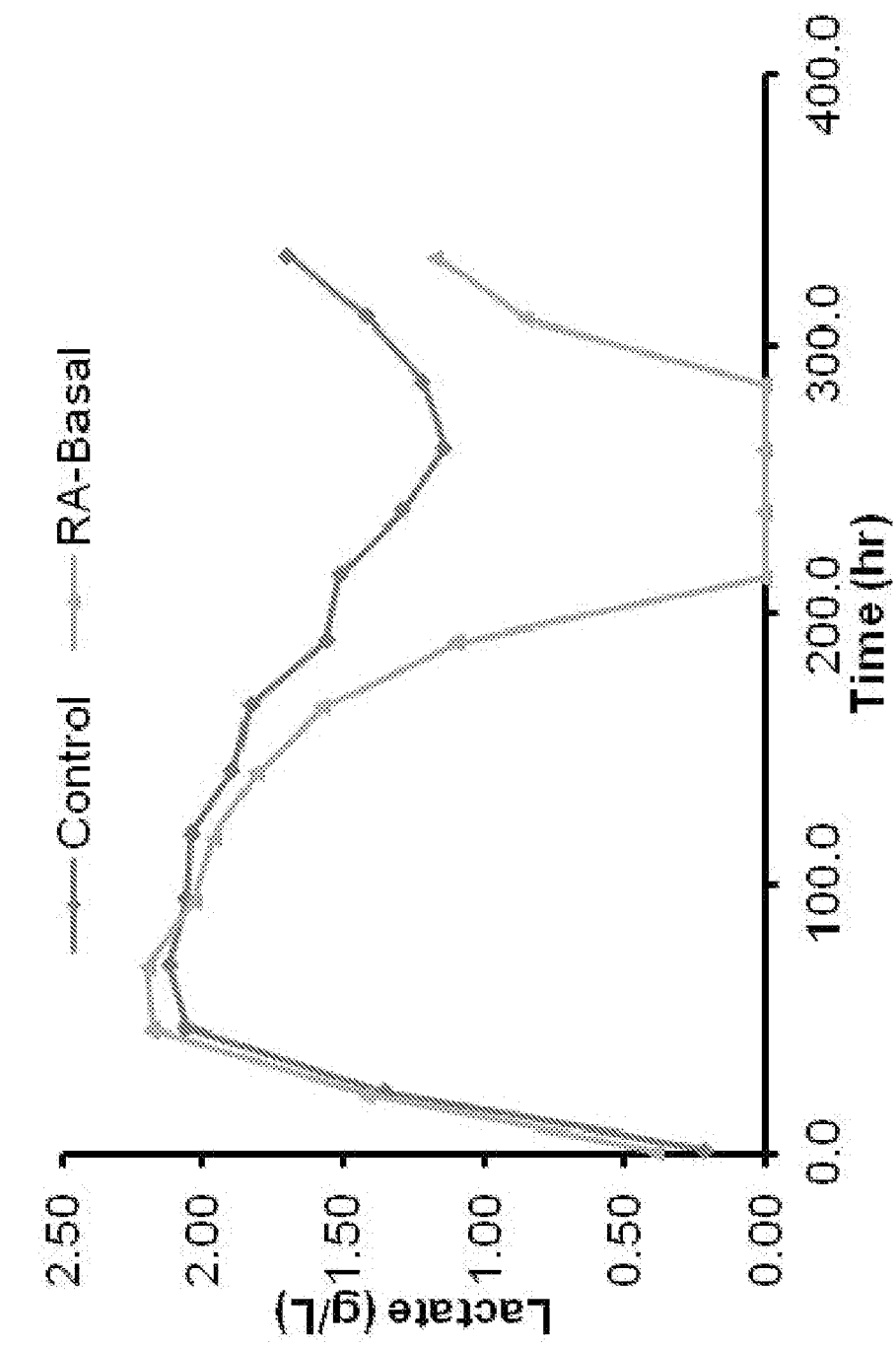

As shown in FIG. 6, the positive rosmarinic effect is maintained when the cell culture is scaled up to 500-liter production run. Adding rosmarinic acid to the basal media at 0.1 mM increased viable cell density and protein titer, and reduced lactate formation.

Myostatin Cells

In another embodiment, the dhfr-negative Chinese Hamster Ovary (CHO) cell line DG44 (Invitrogen Corp. Carlsbad, Calif.) was transfected in order to establish a stable cell line expressing a recombinant human fusion protein.

The transfected CHO DG44 cells expressing the fusion protein was grown in the presence of antioxidants according to the methods of the invention.

As shown in FIG. 7, rosmarinic acid addition to the cell culture either in the basal media at 0.1 mM or feed media at 1 mM or both, the feed and basal media, increased the viable cell density and protein titer, and reduced ammonium formation.

Figure 8:
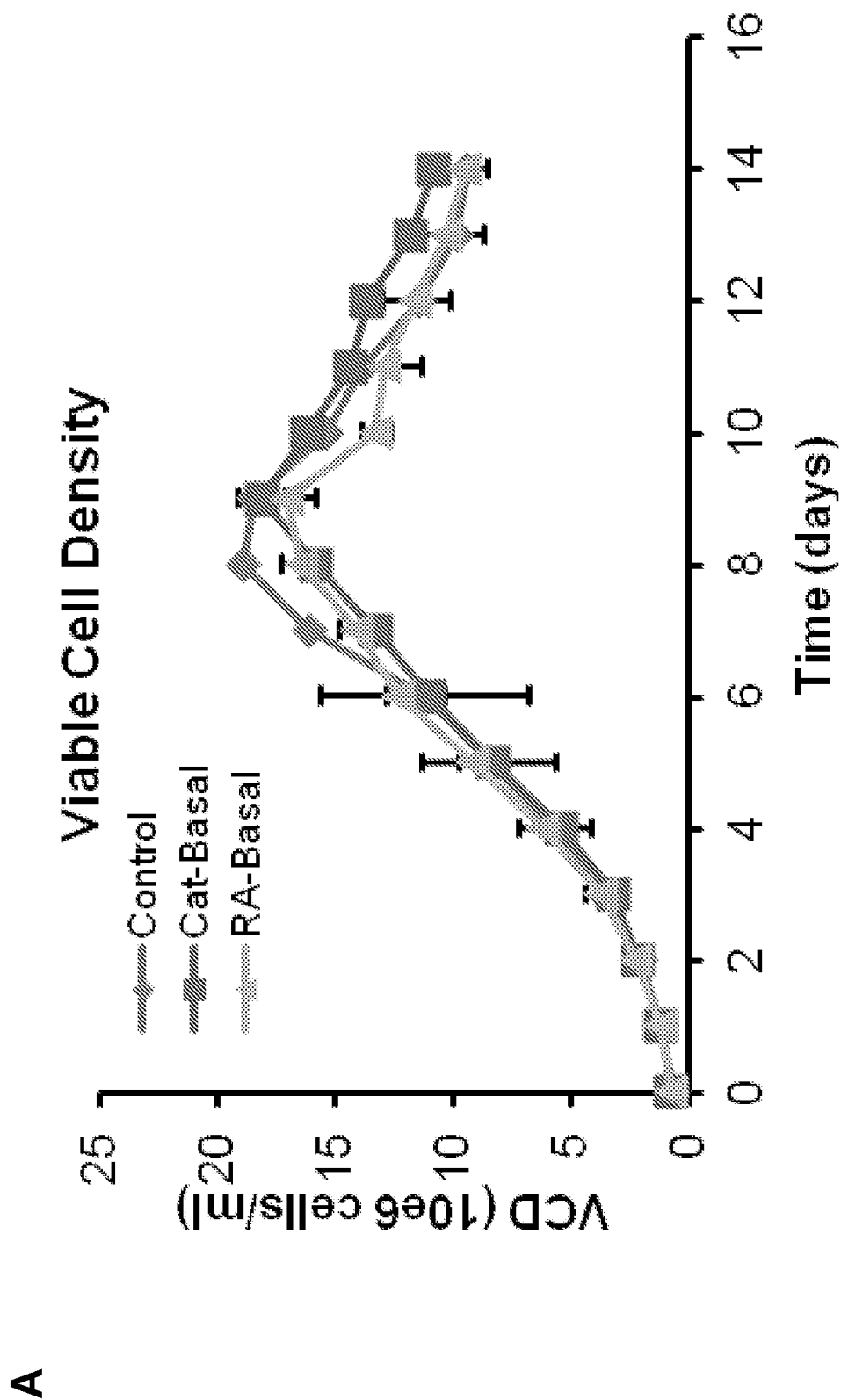
FIG. 8A-C shows the impact of rosmarinic acid (RA-Basal) or catechin (Cat-Basal) addition to basal media B1 at 0.1 mM on (A) viable cell density, (B) cell viability, (C) normalized protein titer and (D) ammonium concentration. The media was used in a 20-liter reactor with myostatin cells together with feed media F3.2.
Figure 8:
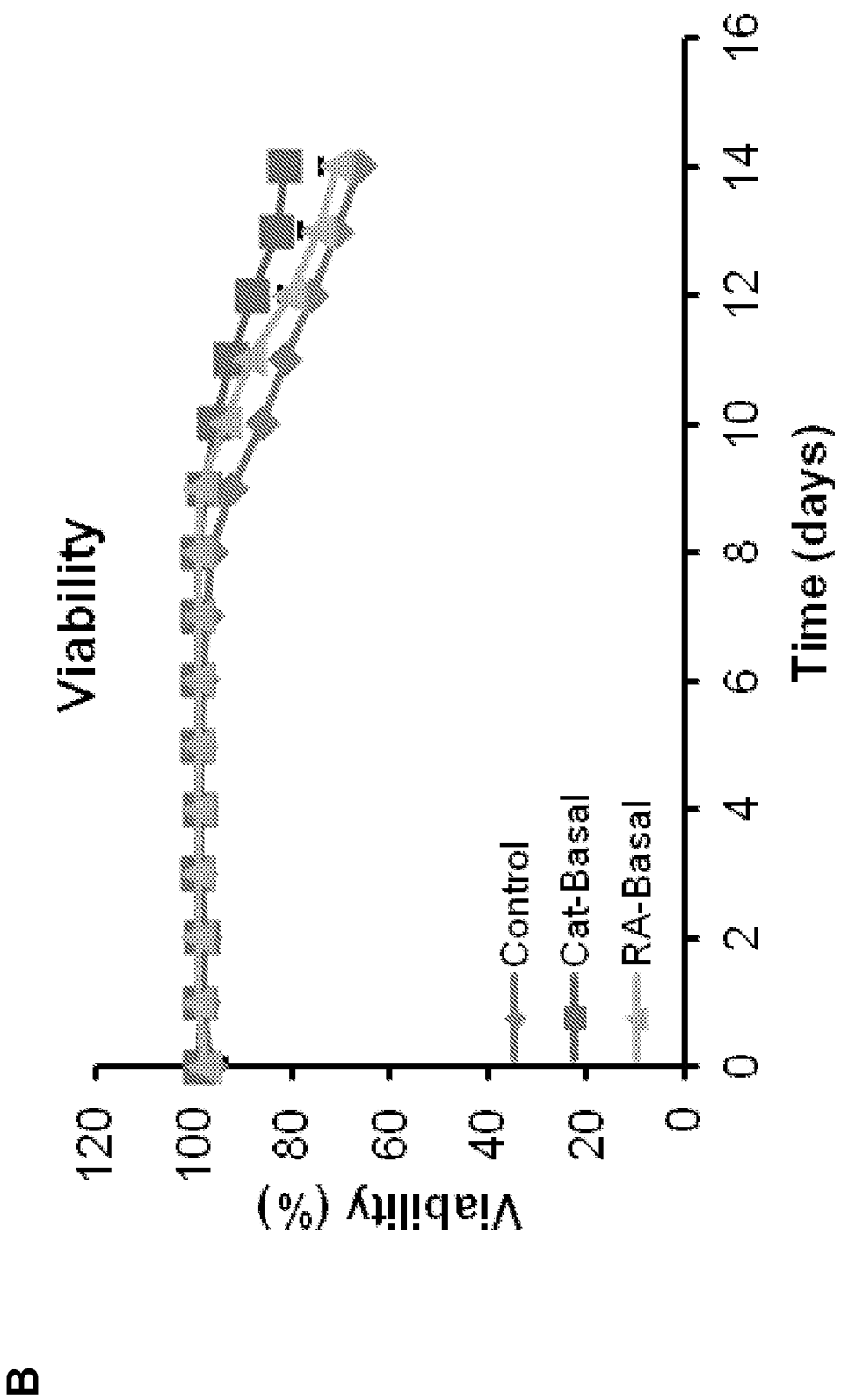
Figure 8:
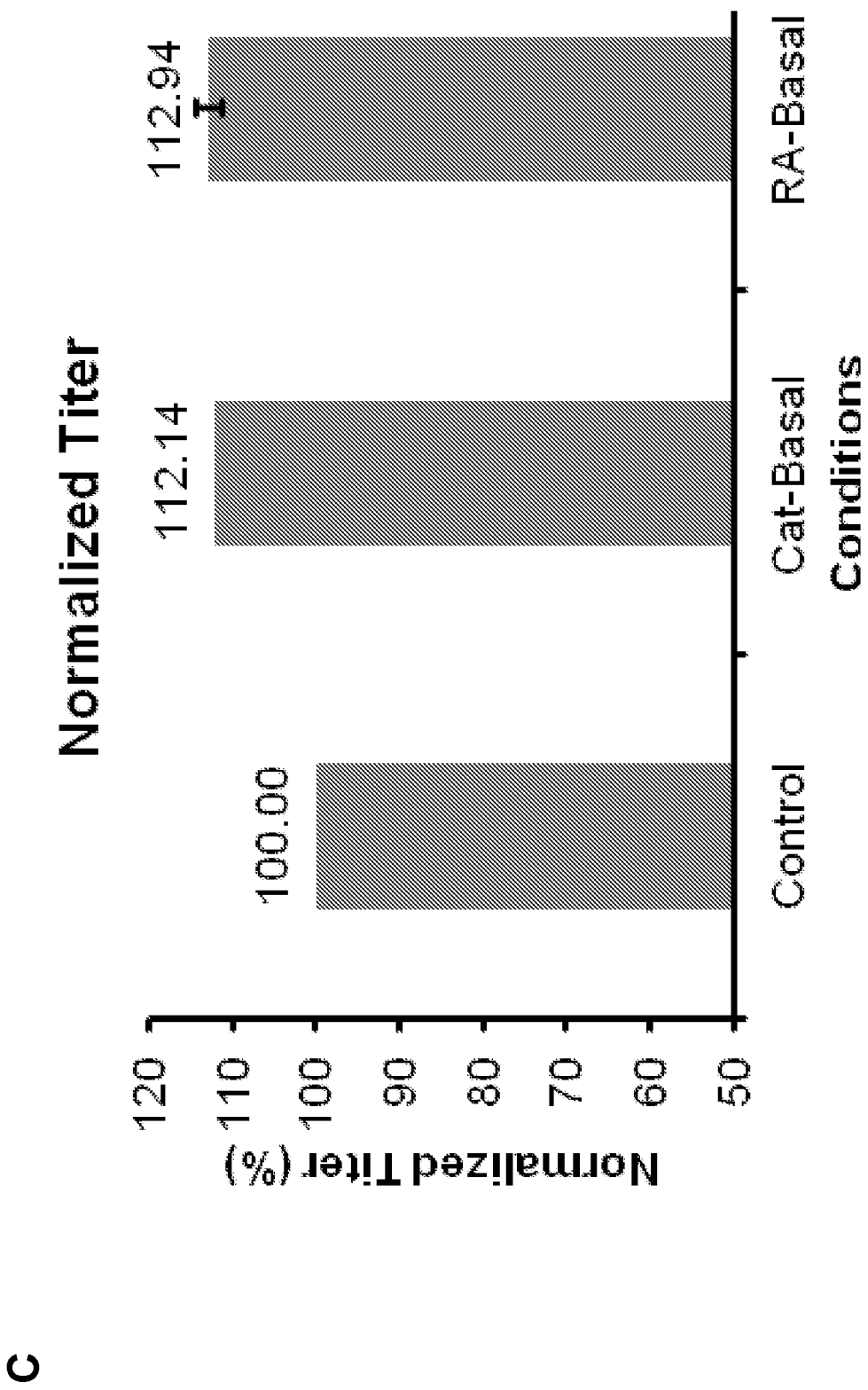

FIG. 8 shows that when the cell culture was scaled up to a 20-liter bioreactor, the positive rosmarinic acid and catechin effect on protein titer was maintained while the viable cell density was not changed by the addition of rosmarinic acid or catechin to the basal media at 0.1 mM.

CD40L Cells

In another embodiment, the dhfr-negative Chinese Hamster Ovary (CHO) cell line DG44 (Invitrogen Corp. Carlsbad, Calif.) was transfected in order to establish a stable cell line expressing a recombinant human fusion protein.

The transfected CHO DG44 cells expressing the fusion protein was grown in the presence of antioxidants according to the methods of the invention.

Figure 9:
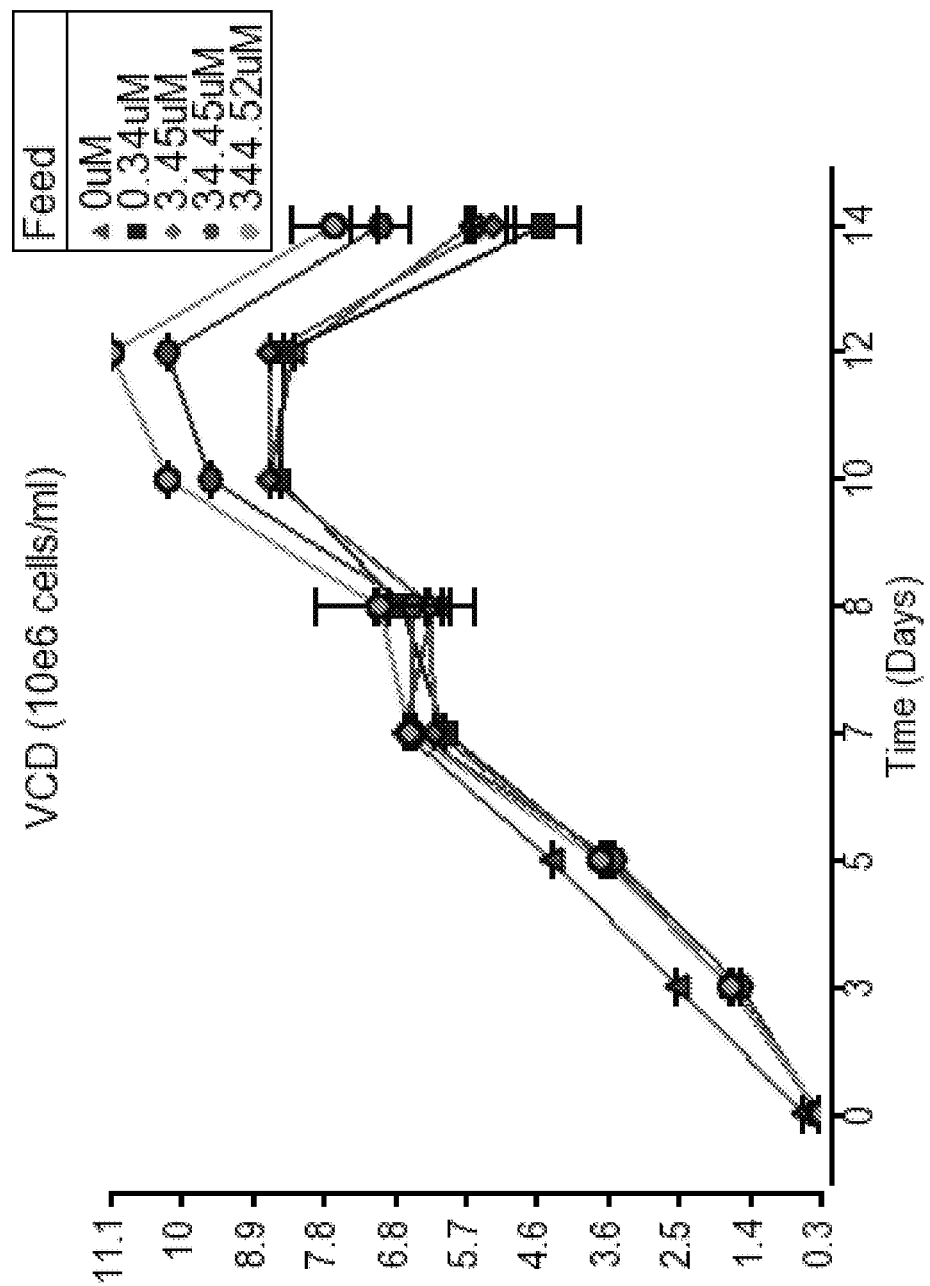
FIG. 9A-C shows the impact of catechin addition to feed media 154A1 at 0.34 µM, 3.45 µM, 34.45 µM or 344.52 µM on (A) viable cell density, (B) cell viability and (C) normalized protein titer. Basal media M17IB without catechin was used for the culture. The media was used in standard shake flasks with aCD40L cells.
Figure 9:
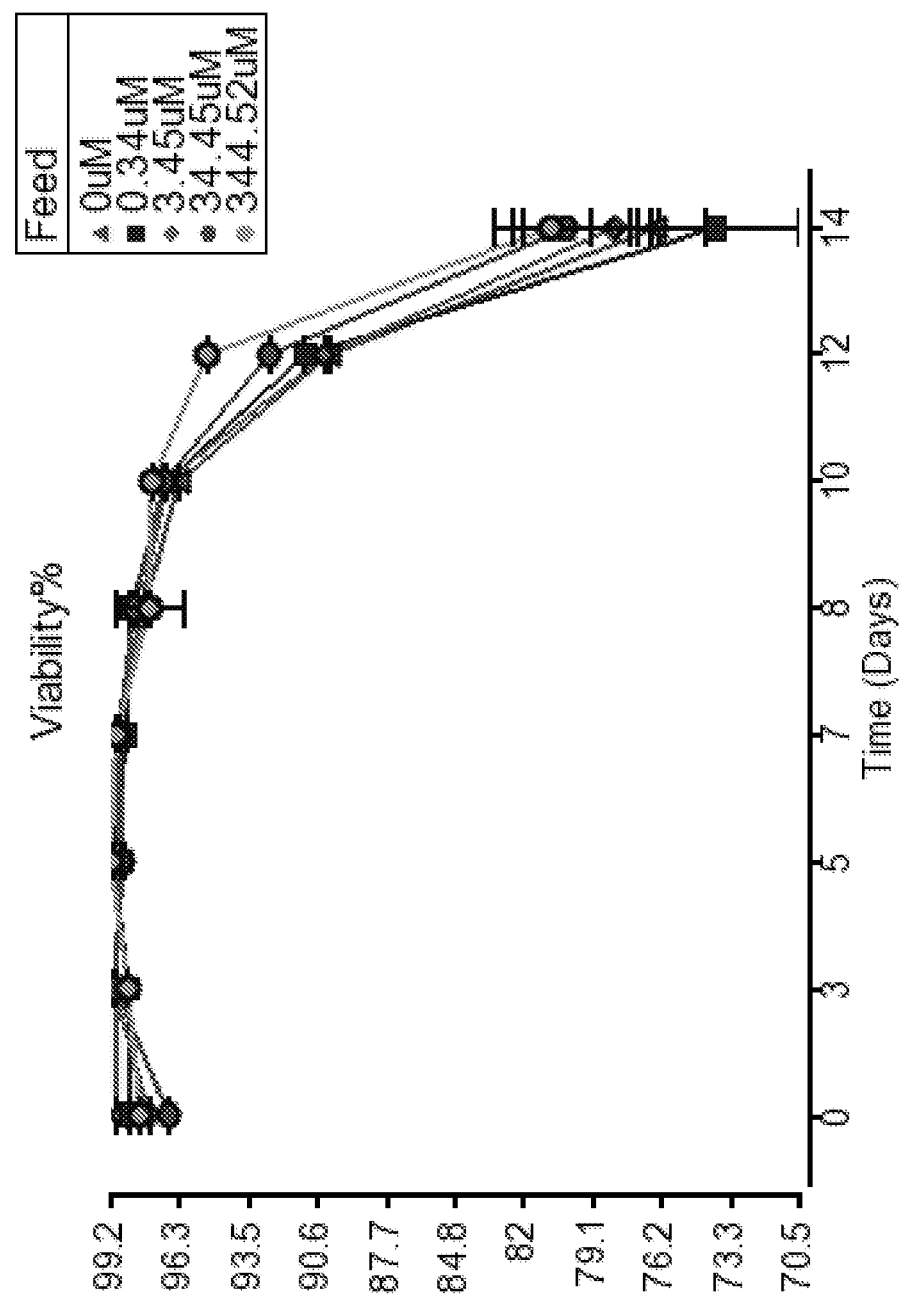
Figure 9:
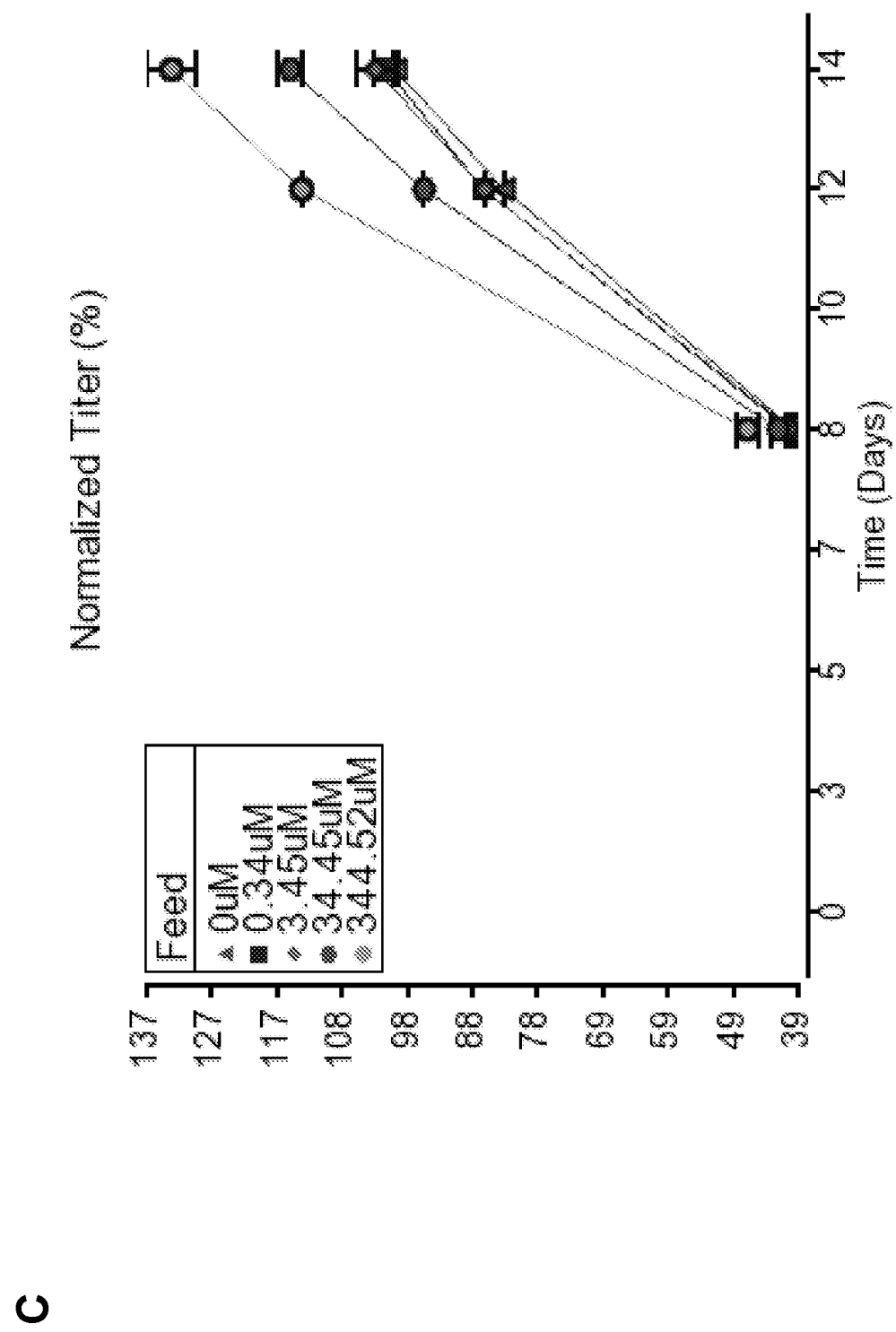

As shown in FIG. 9, the increase in viable cell density and protein titer corresponds to an increase in catechin concentration in the feed media (0.34 µM, 3.45 µM, 34.45 µM and 344.52 µM).

EXAMPLE 1

Cell Culture

Cells were cultured either in 50 ml spin tubes with an initial volume of 25 ml and a shaking speed of 300 rpm; or 250 ml shake flasks with an initial volume of 80~100 ml and a shaking speed of 150 rpm on an orbital shaker with 25 mm throw distance. Temperature for the culture was controlled at constant 37° C. from the beginning of the culture and was shifted to 34° C. when viable cell density reached $10^6$ cells/ml (usually on day 6) and $CO_2$ was controlled at 6%.

A standard fed-batch culture process involved culturing the cells for 14 days with feeding beginning on day 3 at a feeding volume of 3.64% of initial culture volume. All the media used for cultures were chemically defined. Chemically defined feed media M154A1B is an enriched version of feed media F3.2. While the ingredient lists are the same between the two feed media, the concentration of a few of the ingredients is increased. Likewise, chemically defined basal media M17IB is an enriched version of basal media B1. For cultures in 7-liter or 500-liter reactors, dissolved oxygen (DO) was maintained at 50% and pH was controlled between 6.8 and 7.4.

Analyses

Viable cell density (VCD) and cell viability were measured off-line using a CEDEX® automated cell counter (Innovatis AG). Culture samples were also analyzed off-line using a BIOPROFILE® 400 Analyzer to monitor pH, $pCO_2$, $pO_2$, glucose, glutamine, glutamate, lactate, and ammonium (Nova Biomedical Corporation). A Protein A HPLC method was used to measure protein titer, which were reported as normalized values.

We claim:

1. A cell culture process for the production of protein, comprising:
    a) culturing Chinese Hamster Ovary (CHO) cells which produce a protein of interest in cell culture under conditions that allow for protein production; and
    b) adding one or more antioxidant selected from the group consisting of catechin, chlorogenic acid, pelargonidin, quercetin, resveratrol, rosmarinic acid and silibinin to the cell culture,
    wherein protein titer is increased compared to the same cell culture without the antioxidant supplementation.

2. The process according to claim 1, wherein the antioxidant is selected from the group consisting of catechin, chlorogenic acid, quercetin, resveratrol and rosmarinic acid.

3. The process according to claim 1, wherein the antioxidant is catechin or rosmarinic acid.

4. The process according to claim 1 wherein the antioxidant is added to the basal media, feed media or both.

5. The process according to claim 1, wherein the antioxidant is added to the basal media.

6. The process according to claim 1, wherein the antioxidant is added to the feed media.

7. The process according to claim 1, wherein the antioxidant is added to the both the basal and feed media.

8. The process according to claim 1, wherein the antioxidant is added to the feed media, and the feed media is added to the cell culture on a daily basis.

9. The process according to claim 1, wherein the antioxidant is added to the cells in an amount of about 0.0625 mM to 1 mM.

10. The process according to claim 1, wherein the antioxidant is added to the cells in an amount of about 0.1 mM to 1 mM.

11. The process according to claim 1, wherein viable cell density is increased or maintained compared to the same cell culture without the antioxidant supplementation.

12. The process according to claim 1, wherein the antioxidant is rosmarinic acid.

13. The process according to claim 1, wherein the antioxidant is catechin.

14. The process according to claim 5, wherein 0.1 mM rosmarinic acid is added to the basal media.

15. The process according to claim 5, wherein 0.1 mM catechin is added to the basal media.

16. The process according to claim 6, wherein 1 mM rosmarinic acid is added to the feed media.

17. The process according to claim 6, wherein 1 mM catechin is added to the feed media.

18. The process according to claim 7, wherein 0.1 mM rosmarinic acid is added to the basal media and 1 mM rosmarinic acid is added to the feed media.

* * * * *